(12) United States Patent
Ganzer et al.

(10) Patent No.: US 12,115,370 B2
(45) Date of Patent: *Oct. 15, 2024

(54) MOTOR FUNCTION NEURAL CONTROL INTERFACE FOR SPINAL CORD INJURY PATIENTS

(71) Applicant: Battelle Memorial Institute, Columbus, OH (US)

(72) Inventors: Patrick Ganzer, Columbus, OH (US); Samuel Colachis, Columbus, OH (US); Michael Schwemmer, Columbus, OH (US); David A. Friedenberg, Worthington, OH (US); Gaurav Sharma, Lewis Center, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/108,095

(22) Filed: Feb. 10, 2023

(65) Prior Publication Data

US 2023/0271007 A1  Aug. 31, 2023

Related U.S. Application Data

(63) Continuation of application No. 16/729,035, filed on Dec. 27, 2019, now Pat. No. 11,607,545.

(Continued)

(51) Int. Cl.
*A61N 1/36* (2006.01)
*A61N 1/02* (2006.01)
*G06N 3/02* (2006.01)

(52) U.S. Cl.
CPC ......... *A61N 1/36031* (2017.08); *A61N 1/025* (2013.01); *A61N 1/36003* (2013.01); *G06N 3/02* (2013.01)

(58) Field of Classification Search
CPC ............... A61N 1/025; A61N 1/36003; A61N 1/36031; A61N 1/36103; A61N 1/0551;
(Continued)

(56) References Cited

U.S. PATENT DOCUMENTS 11,607,545 B2 * 3/2023 Ganzer .................. A61N 1/025
2018/0154132 A1 6/2018 Bouton et al.

FOREIGN PATENT DOCUMENTS

| EP | 3381506 A1 | 10/2018 |
| WO | WO 2015/063127 A1 | 5/2015 |
| WO | WO 2016/196784 A1 | 12/2016 |

OTHER PUBLICATIONS

International Search Report for PCT Application Serial No. PCT/US2019/068783 dated Apr. 15, 2020.

* cited by examiner

*Primary Examiner* — Jon Eric C Morales
(74) *Attorney, Agent, or Firm* — Lippes Mathias LLP

(57) ABSTRACT

At least one electrical brain signal is received from a patient and is demultiplexed into an efferent motor intention signal and at least one afferent sensory signal (such as an afferent touch sense signal and/or an afferent proprioception signal). A functional electrical stimulation (FES) device is controlled to apply FES to control a paralyzed portion of the patient that is paralyzed due to a spinal cord injury of the patient. The controlling of the FES device is based on at least the efferent motor intention signal. A demultiplexed afferent touch sense signal may be used to control a haptic device. The afferent sensory signal(s) may be used to adjust the FES control.

16 Claims, 13 Drawing Sheets

Related U.S. Application Data

(60) Provisional application No. 62/798,648, filed on Jan. 30, 2019, provisional application No. 62/787,060, filed on Dec. 31, 2018.

(58) Field of Classification Search
CPC ...... A61N 1/36067; G06N 3/02; A61B 5/291; A61B 5/296; A61B 5/369; A61B 5/4064; A61B 2505/09; A61B 5/4058; A61B 5/4035; A61B 5/4029; A61B 5/40
See application file for complete search history.

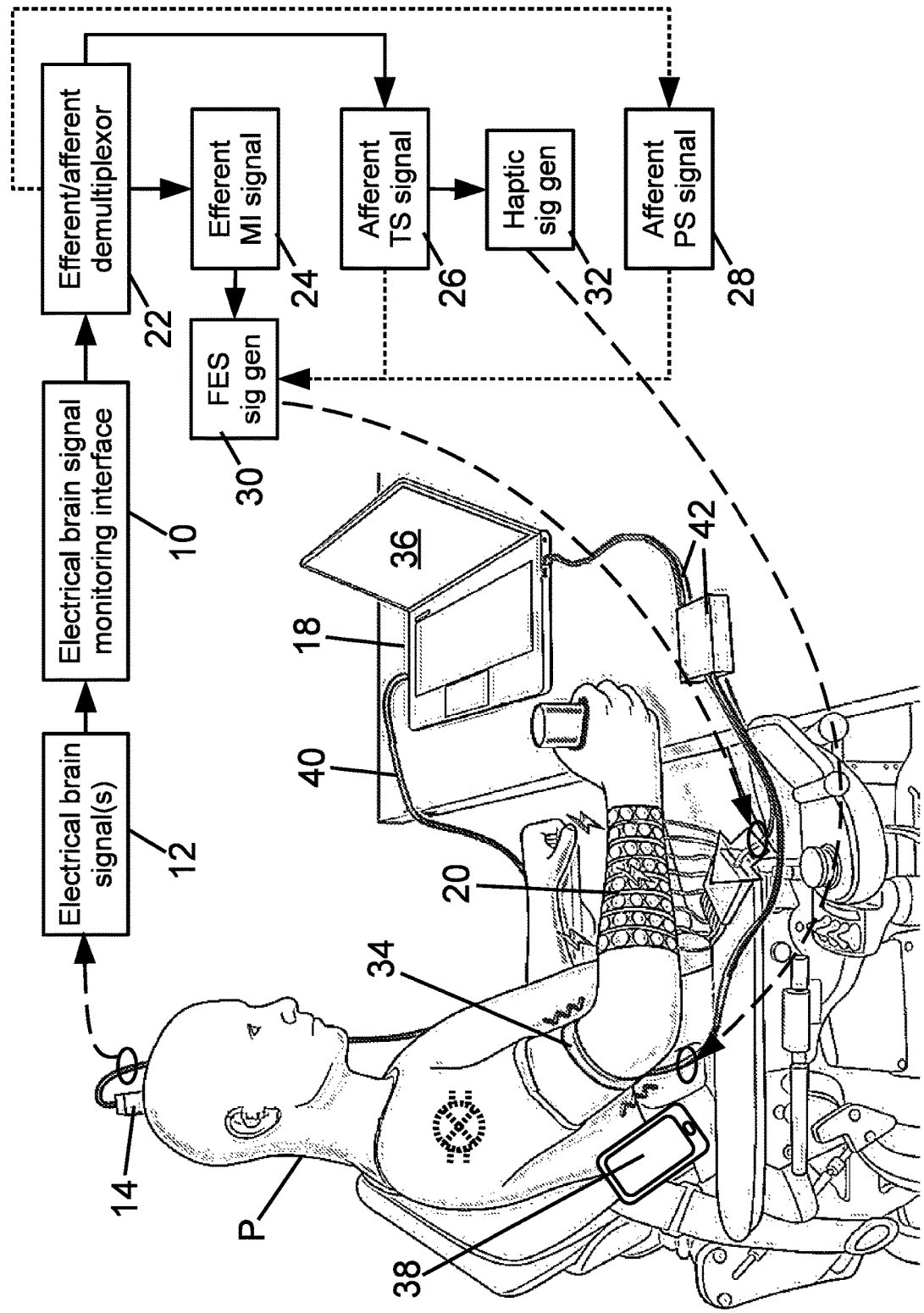

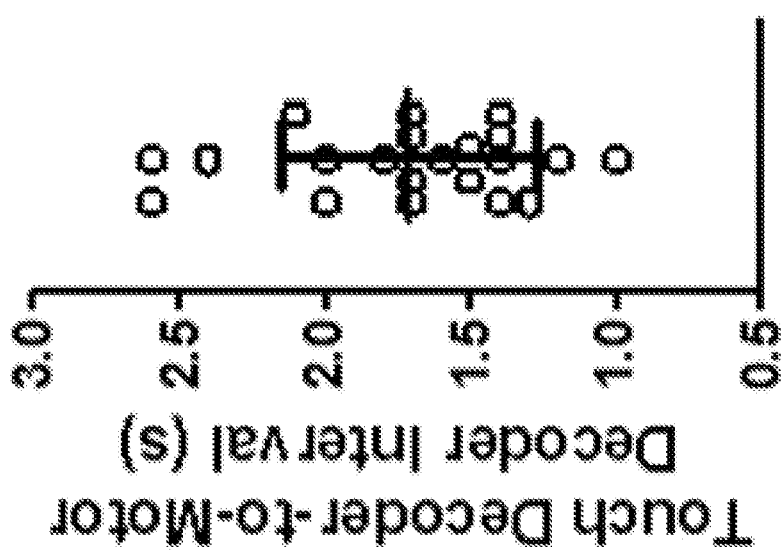
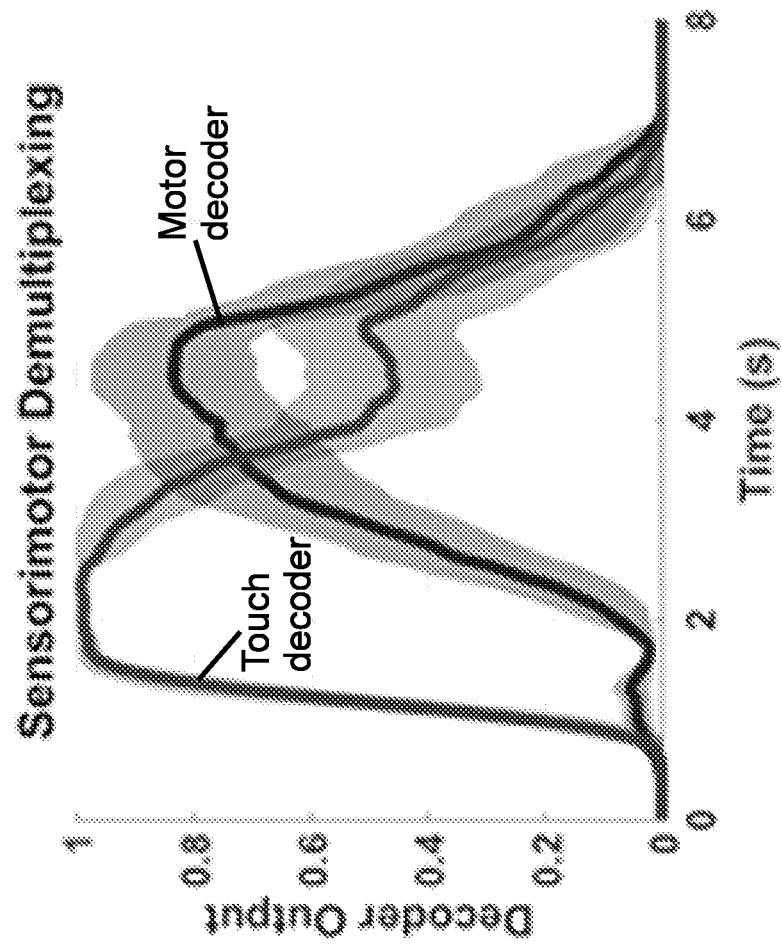
Fig. 10A
Fig. 10B

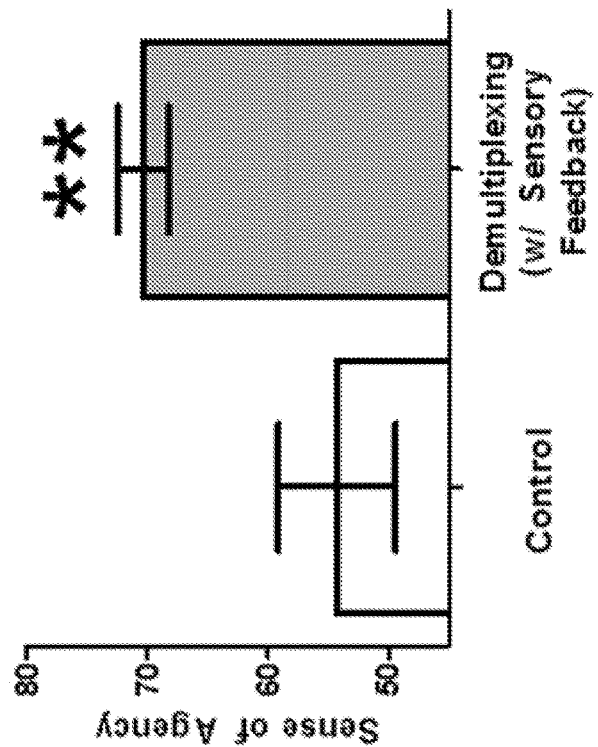
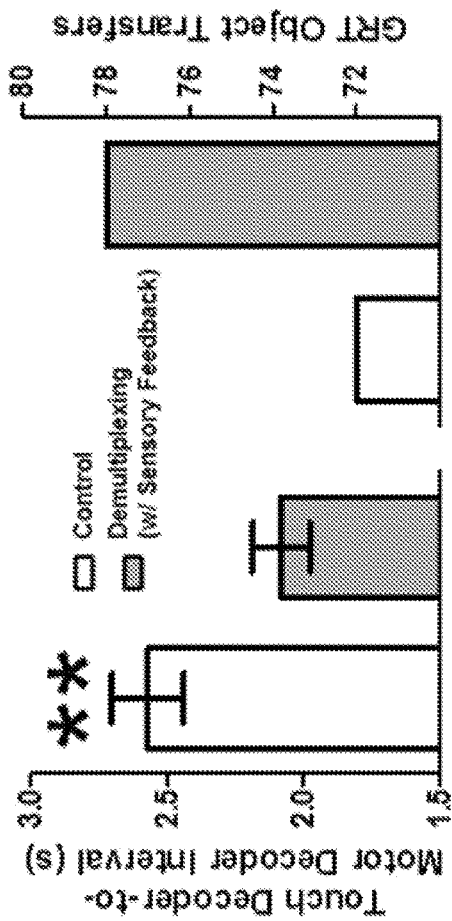
Fig. 11A
Fig. 11B

MOTOR FUNCTION NEURAL CONTROL INTERFACE FOR SPINAL CORD INJURY PATIENTS

This application is a continuation of U.S. application Ser. No. 16/729,035 filed Dec. 27, 2019 and issued as U.S. Pat. No. 11,607,545, which claims the benefit of provisional application No. 62/798,648 filed Jan. 30, 2019, and which claims the benefit of provisional application No. 62/787,060 filed Dec. 31, 2018. Provisional application No. 62/798,648 filed Jan. 30, 2019 is incorporated herein by reference in its entirety. Provisional application No. 62/787,060 filed Dec. 31, 2018 is incorporated herein by reference in its entirety.

BACKGROUND

The following relates to the medical arts, neural-control interface arts, brain-computer interface arts, motor function neural control interface arts, functional electrical neuromotor stimulation arts, neurosensory function assessment and control interface arts, and related arts, and to apparatuses and methods employing same for providing motor functionality to patients with spinal cord injuries.

Over 100,000 individuals in the United States currently live with a cervical spinal cord injury (SCI), in which the cervical spinal cord is partially or wholly severed. Depending upon where the spinal cord injury is located, a lower portion of the patient is paralyzed, e.g. a functionally complete cervical SCI at the C5 level typically results in paralysis of the wrists, hands, and triceps, while a functionally complete cervical SCI at the C6 level typically results in paralysis of the wrist flexors, triceps, and hands. In a functionally complete cervical SCI, motor intention signals for controlling the paralyzed portion of the patient generated by the motor cortex of the brain do not reach the paralyzed portion, and afferent sensory signals from the paralyzed portion are not perceived by the patient.

Various approaches have been developed for assisting such patients. For example, voice recognition software and/or eye movement sensors can be used to allow the patient to control a computer or other electronic devices by voice or eye movements, respectively. However, these patient assistance devices do not replicate the biological motor function lost due to the paralysis.

Another approach is to employ a Brain-Computer Interface (BCI), also sometimes referred to as a Neural-Control Interface (NCI), mind-machine interface (MMI), Direct Neural Interface (DNI), Brain-Machine Interface (BMI), or similar nomenclatures, in conjunction with a Functional Electrical Stimulation (FES) device. The BCI "reads" motor intention (MI) signals generated in the patient's brain (usually in the motor cortex) using electrodes implanted in the brain or contacting the skin adjacent the brain, and controls the FES device on the basis of the MI signals. The FES device includes electrodes implanted in or contacting the skin of the paralyzed portion of the patient (e.g. an FES cuff for use with a paralyzed wrist), so that electrical control signals delivered by these FES electrodes can electrically stimulate motor function. If the MI signals are accurately assessed as to the intended motor function, then the combination of the BCI and the FES device can enable the patient to directly control the paralyzed portion of the body by generating motor intentions in the motor cortex. In other words, the BCI/FES device combination bypasses the cervical SCI and "reconnects" the brain with the motor control nerves so that the patient can move the paralyzed portion using the patient's usual motor intention generated in the motor cortex. Some examples of such BCI/FES device systems are described in Bouton et al., U.S. Pub. No. 2018/0154132 A1 published Jun. 7, 2018 which is incorporated herein by reference in its entirety, and in Bouton et al., U.S. Pub. No. 2018/0154133 A1 published Jun. 7, 2018 which is incorporated herein by reference in its entirety.

Although a BCI/FES device system can mimic thought-driven motor control, a difficulty remains in terms of feedback to the patient. In the case of a functionally complete cervical SCI, the patient cannot perceive sensory signals from the paralyzed portion of the body. In particular, the patient cannot perceive the touch sense due to the functionally complete cervical SCI. Typically, the patient is trained to visually observe the motor operation (e.g. gripping an object with a paralyzed hand) and to rely upon seeing the motor operation (e.g. seeing the hand grip the object) to provide feedback as to success (or failure) of the gripping or other motor operation. However, this approach has some disadvantages. The patient may not visually see the critical point of contact, e.g. the fingertips actually touching the object. The visual perception also does not sensitively capture the strength of the touch, e.g. the finger lightly touching the object versus the finger pressing harder against the object versus squeezing the object hard. Additionally, the patient has had long years of developing motor-sensory feedback based on the touch sense, and it can be difficult for the patient to make the transition to relying upon the different approach of employing visual feedback in a gripping or other motor operation.

The following describes certain improvements.

BRIEF SUMMARY

In accordance with some illustrative embodiments disclosed herein, an apparatus is disclosed for assisting a patient having a spinal cord injury. The apparatus comprises an electrical brain signal monitoring interface, a functional electrical stimulation (FES) device, an electronic processor, and a non-transitory storage medium. The electrical brain signal monitoring interface is configured to record at least one electrical brain signal of the patient. The FES device is configured to connect via FES electrodes with a paralyzed portion of the patient that is paralyzed due to the spinal cord injury and to control the paralyzed portion of the patient by applying FES to the paralyzed portion of the patient via the FES electrodes. The electronic processor is operatively connected with the electrical brain signal monitoring interface to receive the at least one electrical brain signal and with the FES device to control the FES applied to the paralyzed portion of the patient. The non-transitory storage medium stores instructions readable and executable by the electronic processor. The instructions include electrical brain signal demultiplexing instructions that are executable by the electronic processor to demultiplex the at least one electrical brain signal into an efferent motor intention signal and at least one afferent sensory signal. The instructions further include FES control instructions that are executable by the electronic processor to control the FES applied to the paralyzed portion of the patient by the FES device based on at least the efferent motor intention signal.

In accordance with some illustrative embodiments disclosed herein, a method comprises: receiving at least one electrical brain signal from a patient; by an electronic processor, demultiplexing the at least one electrical brain signal into an efferent motor intention signal and at least one afferent sensory signal; and by the electronic processor, controlling a functional electrical stimulation (FES) device to apply FES to control a paralyzed portion of the patient that is paralyzed due to a spinal cord injury of the patient. The controlling of the FES device is based on at least the efferent motor intention signal. The demultiplexing may comprise demultiplexing the at least one electrical brain signal into the efferent motor intention signal and the at least one afferent sensory signal including at least an afferent touch sense signal generated by a touch sense of the paralyzed portion of the patient. In such a case, the method may further comprise, by the electronic processor, controlling a haptic device worn on a portion of the patient where the patient perceives touch sense to deliver a haptic signal to the patient based on the afferent touch sense signal; and/or, the controlling of the FES device may be based on at least the efferent motor intention signal and the afferent touch sense signal. The demultiplexing may comprise demultiplexing the at least one electrical brain signal into the efferent motor intention signal and the at least one afferent sensory signal including at least an afferent proprioception sense signal generated by a proprioception sense of the paralyzed portion of the patient. In such a case, the controlling of the FES device may be based on at least the efferent motor intention signal and the afferent proprioception sense signal. Notwithstanding the foregoing, in some embodiments the controlling of the FES device is based on only the efferent motor intention signal, and is not based on the at least one afferent sensory signal.

In the apparatuses and methods of the immediately two preceding paragraphs, the demultiplexing may comprise applying a machine learning component to demultiplex the at least one electrical brain signal into the efferent motor intention signal and the at least one afferent sensory signal. The instructions may further include instructions to, or the method may further include, by the electronic processor: training the machine learning component to demultiplex the at least one electrical brain signal into the efferent motor intention signal and the at least one afferent sensory signal using labeled training electrical brain signals which are labeled as to motor intention stimuli and sense stimuli. The machine learning component may, for example, be a support vector machine (SVM) or an artificial neural network.

These and other non-limiting aspects of the disclosure are more particularly discussed below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 1 diagrammatically shows an apparatus for assisting a patient having a spinal cord injury.

FIGS. 10A and 10B and FIGS. 11A and 11B illustrate aspects of experiments showing afferent and efferent M1 activity can be simultaneously decoded to enable 'sensorimotor demultiplexing' BCI control and enhancement of sensorimotor function, as described herein.

DETAILED DESCRIPTION

Figure 3:
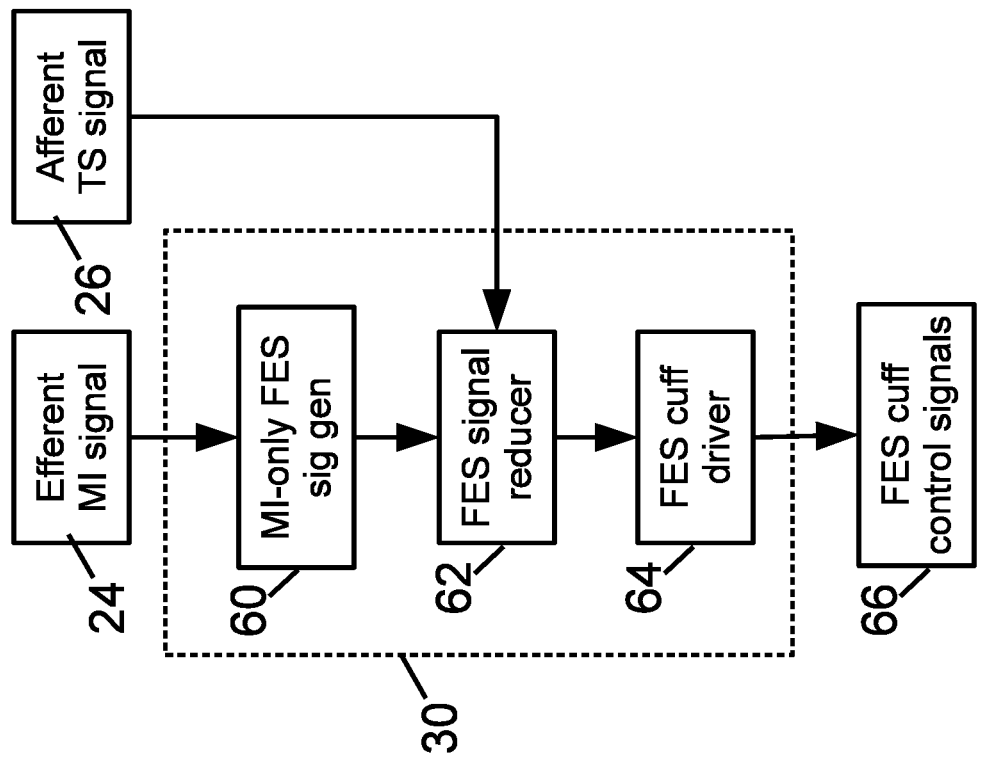
FIG. 3 and FIG. 4 diagrammatically show two illustrative embodiments of the functional electric stimulation (FES) signal generator of the apparatus of FIG. 1.

A more complete understanding of the methods and apparatuses disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

As used herein, the "motor cortex" encompasses all components of the sensorimotor cortex, including sub-regions such as those designated as the primary motor cortex (M1), the primary somatosensory cortex (S1), the premotor cortex, the supplementary motor area (SMA), the posterior parietal cortex, and so forth. As used herein, the term "brain" encompasses the entire brain of the SCI patient, and hence the term "brain" includes, but is not limited to, the motor cortex.

As used herein, terms such as "efferent motor intention signal", "afferent sensory signal", "afferent touch sense signal", and "afferent proprioception sense signal" are referenced to the brain. Hence, "efferent" denotes a signal output by the brain, or in some embodiments more particularly output by the motor cortex of the brain; while, "afferent" denotes a signal received at the brain, or in some embodiments more particularly received by the motor cortex of the brain. For example, an afferent touch sense signal indicates the touch sense signal received at the brain, as opposed to the touch sense signal in the finger or other anatomical structure that senses the touch.

As used herein, the term "electrical brain signal monitoring interface" or similar phraseology denotes a device for measuring or monitoring an electrical brain signal, that is, a signal indicative of electrical activity of the brain, and in some embodiments more particularly indicative of electrical activity of the motor cortex of the brain. These terms are to be broadly construed as denoting brain electrical activity signals in the broadest sense, and are not intended to be limited to detection of any specific type of brain wave or the other narrower interpretation. As used herein, an electrical brain signal encompasses, for example, a signal acquired by as few as a single electrode implanted in the brain or attached to the scalp to detect brain electrical activity.

As used herein, the term "functional electrical stimulus" or the corresponding acronym "FES" is intended to indicate any electrical stimulus applied by one or more electrodes that are implanted into a SCI patient's tissue or organ or anatomical body part or anatomical structure, or attached to skin of such tissue or organ or anatomical body part or anatomical structure, so as to electrically stimulate muscular activity in the issue or organ or anatomical body part or anatomical structure. An FES device is any device including such electrodes which is designed to connect with the SCI patient's tissue or organ or anatomical body part or anatomical structure. In illustrative examples, the FES device is a wrist cuff or sleeve or the like for providing functional electrical stimulation to an SCI patient's wrist and/or hand and/or forearm. As another example, an FES device may be a leg wrap or leg cuff with electrodes for providing functional electrical stimulation to an SCI patient's leg and/or foot.

As noted previously, although a BCI/FES device system can mimic thought-driven motor control, a difficulty remains in terms of feedback to the patient. In the case of a functionally complete SCI, the patient cannot perceive sensory signals from the paralyzed portion of the body. In particular, the patient cannot perceive the touch sense in the paralyzed region due to the functionally complete SCI.

Notwithstanding the foregoing, in approaches disclosed herein, a BCI/FES device system includes an electronic processor programmed to demultiplex at least one electrical brain signal (acquired by one or more electrodes implanted in the brain or attached to the scalp to record brain activity) into an efferent motor intention signal and at least one afferent sensory signal. Although a functionally complete SCI prevents the patient from perceiving sensory signals from the paralyzed portion of the body, this does not mean that afferent sensory signals are not received at (or by) the brain. Residual sensory information is potentially transmitted to the brain of a patient with functionally complete SCI, even though the patient does not consciously perceive the sensations. (Usually an SCI is classified as "complete" based on function alone, e.g. the patient cannot move or feel below spinal level "X". Functionally complete SCI does not necessarily imply an anatomically complete SCI, e.g. there may still be a small amount of spared fibers that reach the brain, and may for example transmit an attenuated touch sense). Moreover, activity in primary motor cortex (M1) and in the primary sensory cortex (S1) may reflect sensorimotor information beyond their primary processing designation, e.g. activity in M1 may be modulated by somatosensory feedback of the neuromotor state of the limb. As shown herein (see Experimental), afferent sensory signals from a paralyzed region impact the electrical brain signals of the motor cortex in spite of the functionally complete SCI, and these afferent sensory signals are at a sufficiently high level to introduce significant noise into the extracted motor intention signal. It is expected that noise due to the afferent sensory signals should be suppressed by demultiplexing the electrical brain signal(s) into an efferent motor intention signal and at least one afferent sensory signal. The resulting (demultiplexed) efferent motor intention signal is thereby "cleaned up" to provide an improved control signal for controlling an FES device to implement the motor intention.

Optionally, the demultiplexed afferent sensory signal(s) may be used for other purposes. In some embodiments, a demultiplexed afferent touch sense signal is used to drive a haptic device worn by the patient on a portion of the body that is not paralyzed due to the SCI. This provides haptic feedback to the patient based on the patient's own touch sense, in spite of that touch sense not being perceptible by the patient.

As noted above, by removing the afferent sensory signal(s) by the demultiplexing, a more "pure" motor intention signal is derived, and in some embodiments this demultiplexed motor intention signal is used by itself for driving the FES device. On the other hand, in some other embodiments the demultiplexed afferent sensory signal(s) may be used to augment the demultiplexed motor intention signal for driving the FES device. For example, the demultiplexed afferent touch sense signal may be used as follows. An FES control signal is first generated based on the (demultiplexed) motor intention signal. This FES control signal is effective to cause the FES device to control the paralyzed portion of the patient to perform a motor action indicated by the motor intention signal. Then, the generated FES control signal is adjusted to reduce a strength of the motor action based on a strength of the (demultiplexed) afferent touch sense signal. For example, in a gripping action, the motor intention signal drives the gripping action, however, when the afferent touch sense signal begins to ramp up as the patient's fingertips begin to touch the object to be gripped, this provides a feedback signal that reduces the strength of the gripping action (e.g., slows the gripping motion) so as to more gracefully grasp the object without producing too much squeezing pressure. Optionally, this is done in conjunction with the aforementioned optional driving of a haptic device in order to concurrently provide the patient with haptic feedback indicating the hand is contacting the object.

As another example (which may be used with any of the above-described examples), the demultiplexed afferent sensory signal(s) may include an afferent proprioception sense signal generated by a proprioception sense of the paralyzed portion of the patient. In some embodiments, the FES applied to the paralyzed portion of the patient by the FES device is controlled based on the motor intention signal and also based on the afferent proprioception sense signal. For example, in a gripping action, the afferent proprioception sense signal may indicate the orientation of the palm of the hand. More specifically, demultiplexed afferent signal for wrist orientation are contemplated to be used to determine which stimulation pattern to use. The patterns change with wrist orientation due to anatomical muscle changes. If the current orientation of the wrist is known, it can inform the FES system which parameters to use for the optimal grip. If the palm is not aligned with the object to be gripped, then the FES control may stimulate wrist muscles to rotate the wrist in order to align the palm with the object, prior to (or along with) driving the hand to perform the gripping action.

With reference to FIG. 1, an apparatus for assisting a patient P having a spinal cord injury (SCI) is diagrammatically shown. (although SCI is the illustrative example, more generally the disclosed approaches are contemplated for use in conjunction with other patients with disrupted sensory and motor neurosignal transmission, such as stroke patients with patients with Parkinson's disease). An electrical brain signal monitoring interface 10 is configured to record at least one electrical brain signal 12 of the patient P via one or more electrodes 14 that are implanted in the brain of the patient P or attached to the scalp of the patient P in order to detect electrical brain activity. The electrodes can be invasive (e.g. implanted underneath the scalp) or non-invasive (e.g. placed on the scalp). The electrode(s) 14 may consist of a single electrode, or may be an array of electrodes. Preferably, the electrode(s) 14 are positioned in order to detect brain activity from the motor cortex of the brain, as motor intention signals can be generated in the motor cortex. In the case of a single electrode implanted in the brain or attached to the scalp, the single electrode is preferably positioned to detect brain activity in the primary motor cortex (M1). In the case of an array of electrodes, various configurations are contemplated. In one approach, the array of electrodes are arranged to span the entire motor cortex and may extend beyond the area of the motor cortex. In another approach, the array of electrodes is arranged entirely within the motor cortex area. In some embodiments, the placement of the electrode(s) 14 is chosen prior to implanting the electrodes by fusing functional magnetic resonance imaging (fMRI) activation maps obtained while the patient attempted movements of the paralyzed anatomy (so as to generate motor intention signals in the motor cortex) co-registered to the preoperative planning MRI. In some actually conducted experiments (see Experimental), the electrode(s) 14 were a Utah 96 channel microelectrode array (Blackrock Microsystems, Inc., Salt Lake, Utah) implanted in the left primary motor cortex of the patient P. These are merely illustrative examples.

The electrical brain signal monitoring interface 10 may be any device that is capable of measuring brain electrical activity detected by the electrode(s) 14. (In some alternative embodiments, it is contemplated to perform this monitoring via peripheral nerve monitoring, e.g. using electrode(s) reading neurological signals conducted along the spinal cord). This may be a commercial electrical brain signal monitoring interface device of a type designed to measure brain waves, or may be another type of neural recording system. The brain electrical activity that is measured may include electrical signals produced by neural activity in the nervous system such as action potentials, multi-unit activity, and local field potential.

In the actually conducted experiments (see Experimental), the electrical brain signal monitoring interface 10 was a Neuroport neural data acquisition system which recorded data from all 96 channels of the Utah 96 channel microelectrode array, sampled at 30 kHz and band pass filtered from 0.3-7.5 kHz using a third order Butterworth analog hardware filter, then digitized and sent to a computer 18 for storage and/or further processing using an interface constructed in MATLAB 2014a (The MathWorks; Natick, MA). Again, these are merely illustrative examples.

The apparatus further includes a functional electrical stimulation (FES) device 20. The FES device contains a set of electrodes that are used to provide electrical stimulation. Very broadly, the term "sleeve" is used to refer to a FES device with a structure that surrounds a body part, for example, an arm, leg, or torso. The sleeve can take the form of a shirt, or pants, if desired. The FES device can also contain sensors for monitoring movement of the body part (position, orientation, acceleration, etc.), which can be used to track the movement of the body part. In the illustrative example and in the actually conducted experiments, the FES device was a multi-channel stimulator and a flexible cuff with up to 130 electrodes that is wrapped around the paralyzed forearm of the patient P, with hydrogel disks (Axelgaard, Fallbrook, CA) placed between the electrodes and skin to act as a conduction enhancer. The electrodes in the actually conducted experiments were 12 mm in diameter and were spaced at 22 mm intervals along the longitudinal axis of the forearm and 15 mm intervals in the transverse direction. Current-controlled, monophasic rectangular pulses (50 Hz pulse rate and 500 µs pulse width) were used to provide electrical stimulation. Pulse amplitudes ranged from 0 to 20 mA and were updated every 100 ms. Stimulator calibrations were performed for each movement using an anatomy-based trial-and-error method to determine appropriate electrode spatial patterns.

It will be appreciated that the FES device is preferably designed for the particular paralyzed anatomy to be stimulated (e.g., a leg wrap or cuff would be suitable for driving a paralyzed leg), and may also optionally be designed and fitted for the individual patient. Some further non-limiting illustrative examples of FES devices are described in Bouton et al., U.S. Pub. No. 2018/0154132 A1 published Jun. 7, 2018 which is incorporated herein by reference in its entirety, and in Bouton et al., U.S. Pub. No. 2018/0154133 A1 published Jun. 7, 2018 which is incorporated herein by reference in its entirety.

The right side of FIG. 1 diagrammatically shows processing operations performed on the electrical brain signal(s) 12 captured by the electrical brain signal monitoring interface 10 in order to generate FES control signal for controlling the FES device 20. As diagrammatically shown, the processing operations include applying an efferent/afferent demultiplexor 22 to demultiplex the electrical brain signal(s) 12 into an efferent motor intention (MI) signal 24 and at least one afferent sensory signal 26, 28. In the illustrative example, afferent sensory signals include an afferent touch sense (TS) signal 26 generated by a touch sense of the paralyzed portion of the patient (e.g., the paralyzed hand of the patient P in the illustrative example), and an afferent proprioception sense signal 28 generated by a proprioception sense of the paralyzed portion of the patient. In illustrative examples, the efferent/afferent demultiplexor 22 comprises a machine learning component that is applied to demultiplex the electrical brain signal(s) 12 into the efferent motor intention signal 24 and the at least one afferent sensory signal 26, 28. Advantageously, the demultiplexor 22 can demultiplex motor intention, touch, and proprioception all simultaneously, and can also demultiplex them separately in time. The machine learning component is trained to demultiplex the electrical brain signal(s) 12 into the efferent motor intention signal 24 and the at least one afferent sensory signal 26, 28 using labeled training electrical brain signals which are labeled as to motor intention stimuli and sense stimuli (see FIG. 5), and the particular afferent sensory signal(s) that is/are demultiplexed by the demultiplexor 22 depends upon which afferent sensory signal(s) are labeled and whose demultiplexing is trained using such labels. In some embodiments, the demultiplexor 22 is only trained to demultiplex the afferent touch sense (TS) signal 26 but not the afferent proprioception sense signal 28 (or, in other embodiments, vice versa). Because the efferent/afferent demultiplexor 22 operates on the electrical brain signal(s) 12, the afferent sensory signal(s) 26, 28 output by the demultiplexor 22 are afferent signals received at (or by) the brain (and more particularly at or by the motor cortex, if the electrode(s) 14 are positioned to read brain activity of the motor cortex). As discussed previously, these afferent sensory signals are generally not perceived by the patient P due to the functionally complete SCI—but they are present at a subconscious level in at least some SCI patients. (It will be appreciated that the approach will not work if the patient's functionally complete SCI is such that no sensory signals from the paralyzed body part reach the brain, but this is not the case in at least some SCI patients, even with nominally "complete" SCI).

Although not illustrated, it is also contemplated that additional afferent sensory signals may be demultiplexed, such as visual sensory signals to the extent that such may be present in the motor cortex.

As further diagrammatically shown in FIG. 1, the efferent motor intention (MI) signal 24 is input to an FES control signal generator 30 to generate control signals for controlling the FES device 20 to drive the paralyzed body portion (e.g., the hand and possibly also the wrist of the patient P in the illustrative example) to perform the action indicated by the motor intention signal 24. Because the demultiplexor 22 has separated the motor intention signal 24 from the afferent sensory signal(s) 26, 28, the motor intention signal 24 is less noisy (since the afferent sensory signal(s) 26, 28 constitute noise superimposed on the motor intention signal generated in the motor cortex). Optionally, the afferent sensory signal(s) 26, 28 may be used in other ways. For example, the afferent touch sense signal 26 may be used to reduce the gripping force (see FIG. 3), and/or the afferent proprioception sense signal 28 may be used to align the palm of the hand with an object to be gripped (see FIG. 4) and/or to change stimulation parameters to account for anatomical musculature changes during pronation/supination. As further illustrated in FIG. 1, the afferent touch sense signal 26 may optionally also be used by a haptic device drive signal generator 32 to drive a haptic device 34 worn by the patient on a portion of the body that is not paralyzed by the functionally complete SCI. (In the illustrative example of a functionally complete SCI at the C5/C6 level, the hand and wrist are typically paralyzed, but the upper arm where the illustrative haptic band 34 is worn is usually not paralyzed and the patient P can sense the vibration (i.e. the haptic signal) produced by the haptic band 34 worn on the upper arm). While a haptic device 34 is used in the illustrative example, other devices for producing a human-perceptible feedback signal indicating the strength of the afferent touch sense signal 26 are contemplated, such as displaying the strength as a length of a bar shown on a computer display 36 or so forth.

The various signal/data processing 22, 30, 32 is suitably performed by an electronic processor, such as the computer 18 (as in the actually conducted experiments) or a cellular telephone (cellphone) 38, and/or so forth. Employing the cellphone 38 as the electronic processor advantageously could facilitate patient mobility, e.g. the cellphone 38 may be carried in a holster or the like. In the actually conducted experiments, the electrical brain signals 12 were carried by a wire bundle 40 to the computer 18, and wiring 42 was provided for distributing the FES control signals for the FES electrodes of the FES device 20 and the haptic control signal to the haptic device 34. In the case of using the cellphone 38, wireless communication of the electrical brain signal(s) 12 and FES and haptic control signals may be preferable, e.g. using Bluetooth™ or another short-range wireless communication protocol.

As is known in the computer arts, to configure the electronic processor (e.g. computer 18 or cellphone 38) to perform the described tasks, suitable software is employed to program the electronic processor 18, 38 to perform these tasks. Hence, a non-transitory storage medium (not shown) stores instructions that are readable and executable by the electronic processor 18, 38 to perform these tasks. The non-transitory storage medium may, for example, include a Read-Only Memory (ROM), flash memory, or other electronic storage (e.g., the internal memory of the cellphone 38); a hard disk or other magnetic storage (e.g. of the computer 18); an optical disk or other optical storage; various combinations thereof, and/or so forth. The instructions may (byway of non-limiting illustrative example) include: electrical brain signal demultiplexing instructions that are executable by the electronic processor 18, 38 to demultiplex the electrical brain signal(s) 12 into the efferent motor intention signal 24 and the at least one afferent sensory signal 26, 28; FES control instructions that are executable by the electronic processor 18, 38 to control the FES applied to the paralyzed portion of the patient by the FES device 20 based on at least the motor intention signal 24; touch sensory feedback instructions that are executable by the electronic processor 18, 38 to control the haptic signal delivered to the patient via the haptic device 34 based on the afferent touch sense signal 26; and/or so forth.

The efferent/afferent demultiplexor 22 is trained to perform the demultiplexing using labeled data. It is contemplated that this training may be done once for all patients. However, due to the individualized nature of brain neural activity, it is expected that better FES control performance will be achieved by individually training the efferent/afferent demultiplexor 22 for the individual patient P with which the efferent/afferent demultiplexor 22 is to be used. (This may be ab initio training, or may be a type of update training, i.e. tuning, of a machine learning component that is initially/previously trained on population data, that is, labeled data acquired for a population of patients with similar SCI). Hence, the instructions stored on the non-transitory storage medium may further include machine learning instructions that are executable by the electronic processor 18, 38 to train the machine learning component (implementing the efferent/afferent demultiplexor 22) to demultiplex the electrical brain signal(s) 12 into the efferent motor intention signal 24 and the at least one afferent sensory signal 26, 28 using labeled training electrical brain signals (of the individual patient P in the case of individualized training) which are labeled as to motor intention stimuli and sense stimuli.

Figure 2:
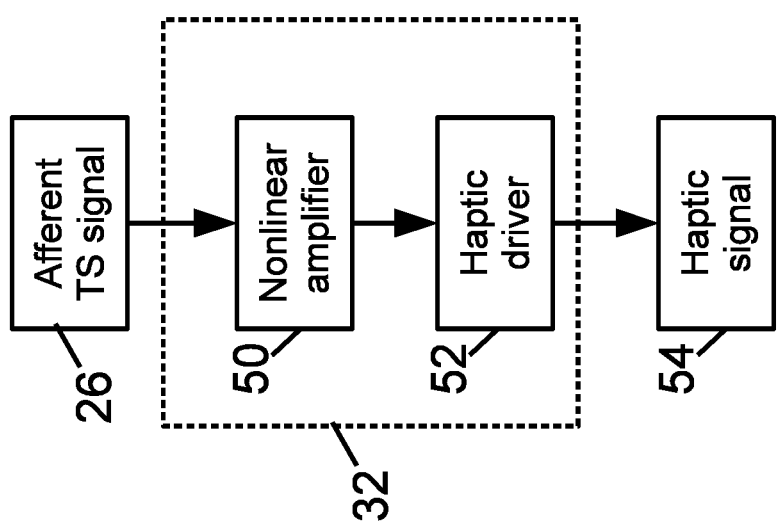
FIG. 2 diagrammatically shows an illustrative embodiment of the haptic signal generator of the apparatus of FIG. 1.

With reference now to FIG. 2, an illustrative example of the optional haptic feedback aspect is described in further detail. The afferent touch sense signal 26 is amplified by a nonlinear (or, in another embodiment, a linear) amplifier 50, and the amplified output is input to a haptic device driver 52 to generate a haptic signal 54 for driving the haptic device 34. The gain, offset, and/or other parameters of the nonlinear amplifier 50 may be adjusted by trial-and-error to tune the haptic feedback to a level that the patient P finds to be most helpful.

With reference now to FIG. 3, an illustrative example of the optional afferent touch sense feedback in adjusting the FES control is described. The illustrative example employs a FES signal generator 60 of a type used in FES control employing only the motor intention signal (that is, without any efferent/afferent demultiplexing). Thereafter, the afferent touch sense signal 26 is used in an operation 62 to reduce the FES signal, that is, to reduce the strength of the illustrative gripping action, in response to an increasing magnitude of the afferent touch sense signal. The operation 62 may, for example, apply no reduction so long as the afferent touch sense signal 26 is below some threshold (corresponding to some percentage over the root-mean-square noise level of the afferent touch sense signal 26, for example). When the afferent touch sense signal 26 increases above this threshold (indicating the fingers are beginning to touch the object to be gripped) the operation 62 begins to reduce the rate of closure of the hand being driven to perform the gripping operation. As the afferent touch sense signal 26 continues to increase, the operation 62 further reduces the rate of closure of the hand being driven to perform the gripping operation. When the afferent touch sense signal 26 increases above an upper threshold (indicating the hand has fully grasped the object) then the operation 62 reduces the rate of closure of the hand to zero and causes it to maintain its current grip force. This is merely an illustrative example, and other types of feedback control of FES-driven actions may be employed depending upon the type of action and the type of available afferent touch sense signal. The FES cuff driver 64 then generates the FES cuff control signals 66 for driving the FES device 20 (see FIG. 1) in accordance with the generated and reduced FES signal.

Figure 4:
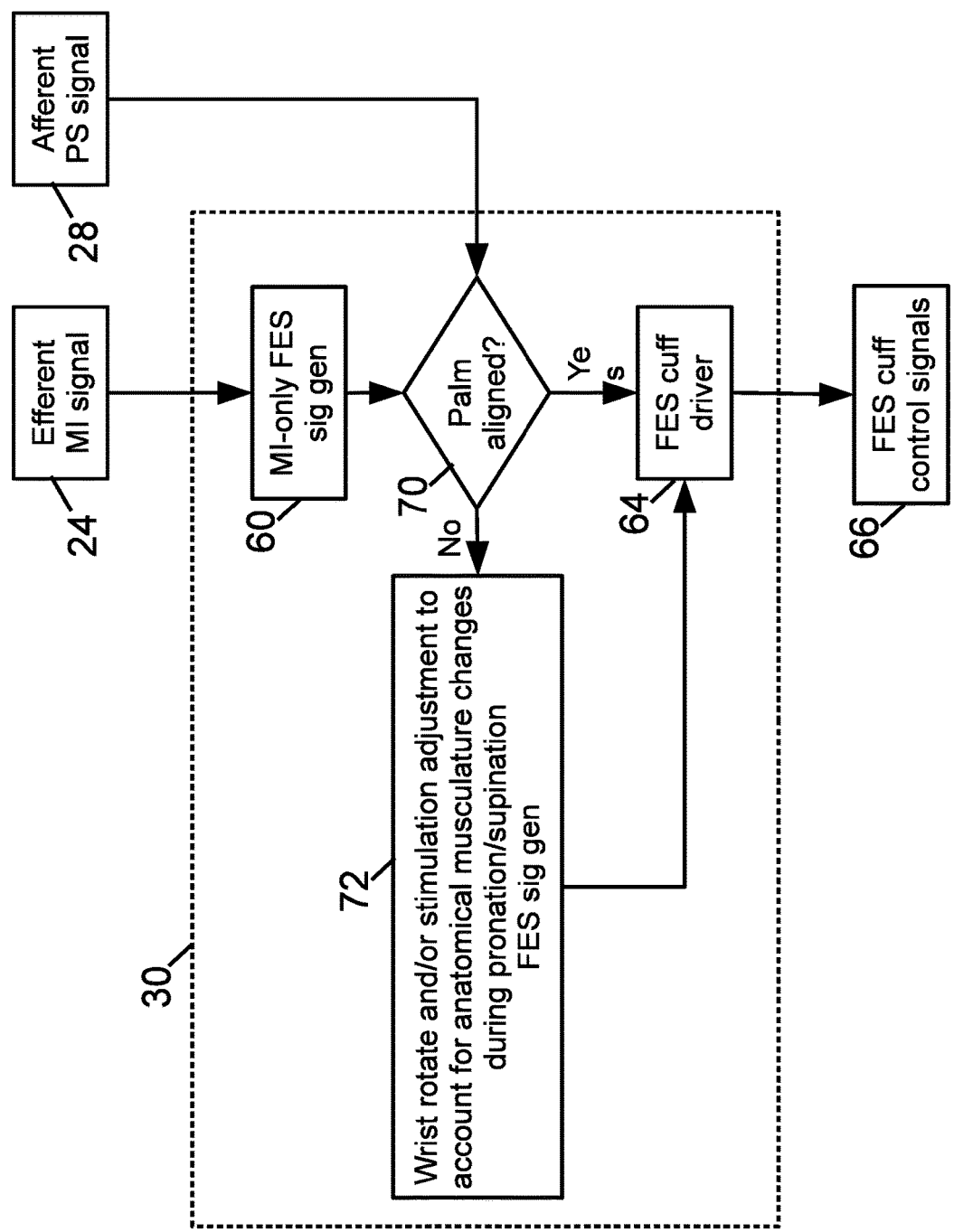

With reference now to FIG. 4, an illustrative example of the optional afferent proprioception sense feedback in adjusting the FES control is described. The illustrative example again employs the FES signal generator 60 already described with reference to FIG. 3. At a decision operation 70, the afferent proprioception sense signal 28 is used to assess whether the palm of the hand is oriented correctly for grasping the object. For example, if the object is a can or glass containing a drink, then the palm should be oriented vertically in order to grasp the sides of the can or glass. If the palm is determined to be oriented properly at decision 70, then FES cuff driver 64 generates the FES cuff control signals 66 for driving the FES device 20 as already described with reference to FIG. 3. On the other hand, if the palm is not correctly oriented (e.g. palm facing up, or palm facing down) then in an operation 72 an additional FES signal component is added in order to cause the FES device 20 to rotate the wrist into position for grasping the can or glass, and this additional wrist drive FES signal is also output by the FES cuff driver 64. Additionally or alternatively, the demultiplexed afferent signals may be used to adjust stimulation parameters based on wrist orientation.

It should be appreciated in understanding the flow diagrams of FIGS. 2-4 that the processing in the dashed boxes is performed by the haptic signal generator 32 (for FIG. 2) or the FES signal generator 30 (for FIGS. 3-4), and that the processing diagrammatically shown in FIGS. 2-4 is performed in a continuing loop, so that for example the FES signal reduction 62 of FIG. 3 may be initially zero for the first iterations, until the continued FES-driven closure of the hand causes the fingers to begin contacting the object whereupon later iterations of the FES signal reduction 62 begin to reduce the closure rate of the hand.

Figure 5:
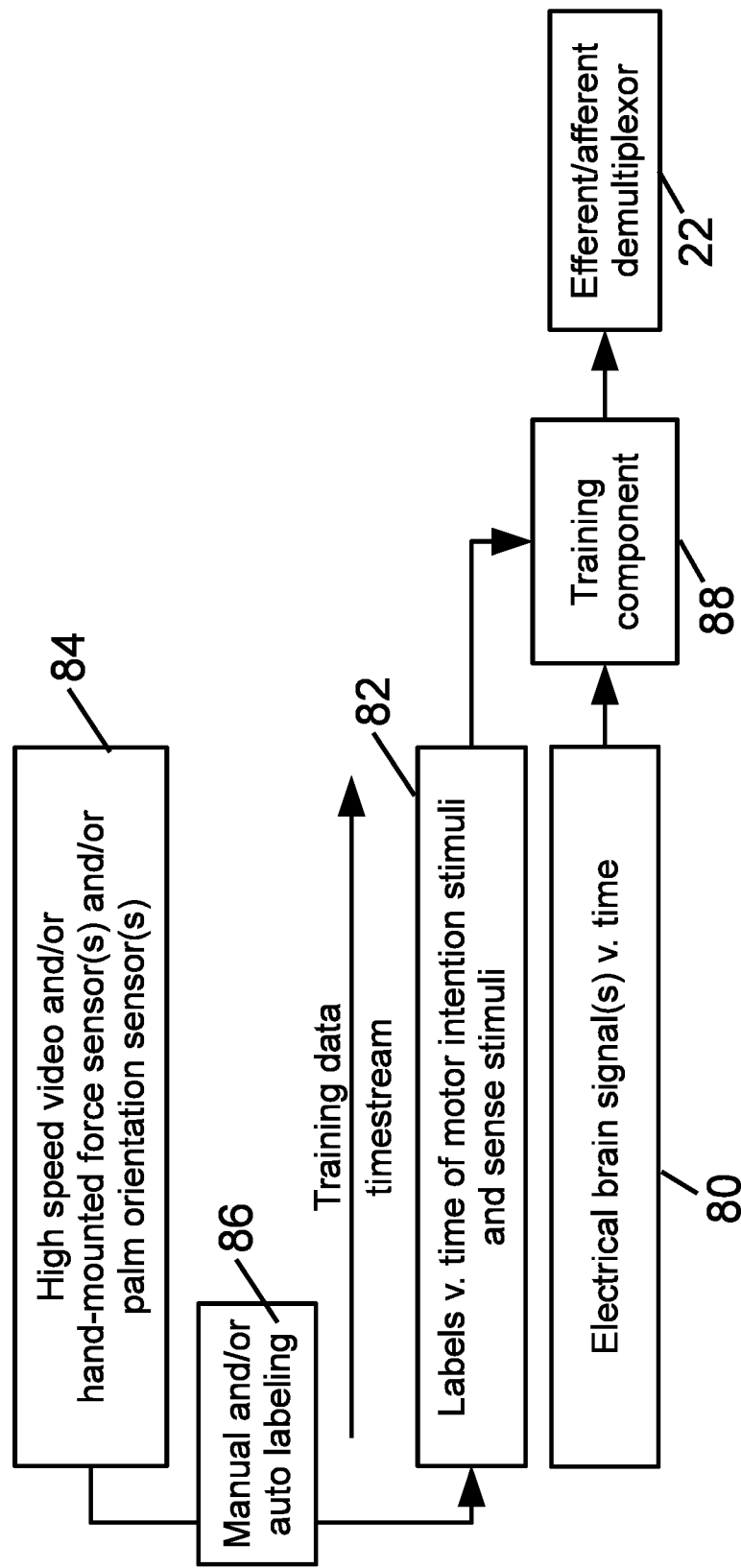
FIG. 5 diagrammatically shows a training system for training the efferent/afferent demultiplexor of the apparatus of FIG. 1.

With reference to FIG. 5, the training of the machine learning component that implements the efferent/afferent demultiplexor 22 is described. The machine learning component may, by way of non-limiting illustration, be a support vector machine (SVM, as in the actually conducted experiments), an artificial neural network (e.g. a deep neural network, DNN, a convolutional neural network, CNN, or so forth), or other type of machine learning system. The parameters adjusted by the training depend upon the type of machine learning component employed. For example, in an SVM the parameters that are adjusted during the training include the hyperplane parameters, e.g. parameters of a vector w oriented normal to the hyperplane, and a plane offset b. In the case of an artificial neural network, the parameters that are adjusted during the training are typically parameters (e.g. weights, activation values, et cetera) of the neurons of the various layers of the artificial neural network. The training adjusts the parameters of the machine learning component so that when the machine learning component processes labeled training data the outputs (in the instant case, the efferent motor intention signal 24 and the afferent sensory signal(s) 26, 28) optimally match ground-truth labels provided with the training data. To provide individualized responses, the training data may comprise electrical brain signal(s) versus time 80 measured for the individual patient P for which the demultiplexor 22 is being trained. In other words, the training data 80 corresponds to the electrical brain signal(s) 12 of FIG. 1 measured as a function of time (i.e. a data stream of timestamped electrical brain signal samples. The ground truth labels 82 are the motor intention stimuli (that is, what the patient P intended to do with the paralyzed body part at a given time) and the sense stimuli. This information can be obtained in various ways, e.g. high speed video and/or force sensor(s) 84 may be provided in conjunction with manual and/or automatic labeling 86. Some illustrative labeling examples follow.

In one approach, force sensors are disposed on the fingers of the patient P. When the patient grips an object using the BCI/FES device system, these force sensors detect when the fingers touch the object being gripped, and the data stream of timestamped force sensor signal samples are aligned in time with the data stream 80 of electrical brain signal samples to identify when a touch stimulus occurs. This approach is well suited for automated generation of touch sense labels. For the proprioception sense signal, it is contemplated to employ a magnetometer and/or accelerometer mounted to the hand to measure its orientation in real time, again facilitating automated generation of proprioception sense labels (e.g. palm up/down/sideways/specific angle/etc).

In another approach, high speed video is acquired as the patient P performs an action using the paralyzed body part driven by the BCI/FES device system. The high speed video is acquired as the patient P grips an object using the BCI/FES device system. The video frames are timestamped and can be retrospectively analyzed to determine when the fingers began touching the object being gripped, and/or to determine the palm orientation, and/or so forth. This could be done automatically with suitable (complex) video image analysis, or may be done manually.

The motor intention labels can be similarly obtained from video or another timestamped input. For example, the patient P can be instructed to grip an object when a light within the patient's field of vision comes on, and the ground truth motor intention can then be set to the time when the light comes on (as measured by a timestamped control signal of the light, or by timestamped video frames that capture the light). To account for any time lag between the patient seeing the light come on and actually initiating the motor intention in the motor cortex, the training can include a single delay parameter that is optimized along with the machine learning component.

With the training data 80 collected and a corresponding time stream of ground truth labels 82 provided, a training component 88 consumes this training dataset 80, 82 to train the SVM, artificial neural network, or other machine learning component that implements the efferent/afferent demultiplexor 22. The training component 88 can employ any suitable training algorithm, e.g. backpropagation in the case of artificial neural network training. The training algorithm(s) applied are chosen based on the type of machine learning component (e.g. SVM or particular type of artificial neural network). As is known in the machine learning arts, some training data may be kept aside and used as validation data to test the trained efferent/afferent demultiplexor 22.

Experimental

In the following, some actually conducted experiments demonstrating various aspects of the methods and apparatuses disclosed herein are described. These experiments generally employ the system depicted in FIG. 1.

A study was conducted of sensorimotor neural signal demultiplexing, to enable a BCI system capable of simultaneously controlling multiple assistive devices for restoring both motor and sensory function. All experiments were performed in a chronically paralyzed participant with a C5/C6 SCI. Experiments first assessed the participant's residual hand sensory function. He was unable to perceive sensory stimuli to skin innervated below spinal level C6. This sensory impairment was also present during FES-mediated object grip. For example, the participant operated below chance when asked to report if he was gripping an object in the absence of visual feedback, a significant sensory impairment further contributing to motor dysfunction.

Experiments next investigated whether this residual sensory information could significantly modulate neural activity following skin stimulation. Sensory stimuli robustly modulated contralateral M1. Stimulation of skin innervated from above or at the C5/C6 SCI evoked time-locked neural modulation, lasting ~10 times longer than the stimulus duration (FIG. 6B) (FIG. 6C: $F[3,24]=7.6$, $p<0.001$; FIG. 6D: $F[3,24]=8.7$, $p<0.001$). Stimuli to skin innervated from below the SCI (index and middle) evoked modest neural modulation in M1. As expected, separate control experiments revealed no M1 activation following sensory stimuli to the left arm, ipsilateral to the M1 recording array. In lower frequencies of neural activity (5-20 Hz), sensory responses also propagated across the array away from primary somatosensory cortex (S1) via a traveling wave front. Sensory stimuli also led to a ~2-fold increase in traveling wave probability, only for semi-intact sensory circuits (forearm & thumb, FIG. 7B; $F[3,48]=9.1$, $p<0.001$). These results show that sensory stimuli to skin innervated from both above and below the SCI significantly modulates M1 in the patient.

Figure 8A:
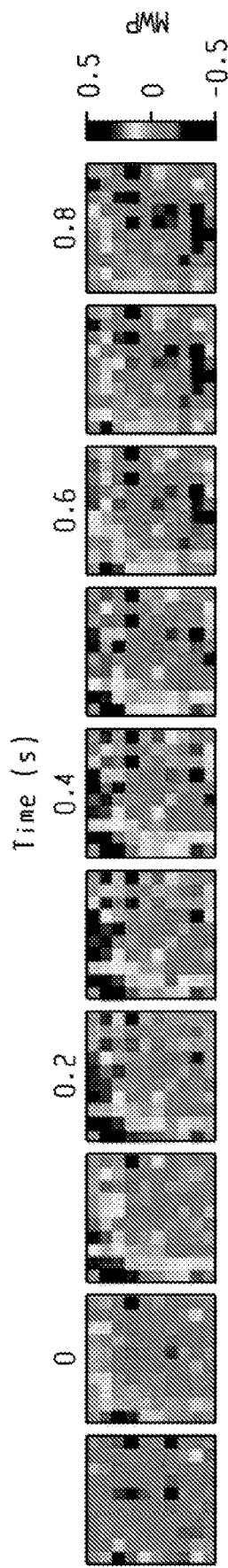
FIGS. 8A, 8B, and 8C illustrate aspects of experiments showing evoked sensory activity in M1 is decodable across skin locations, as described herein.
Figure 8B:
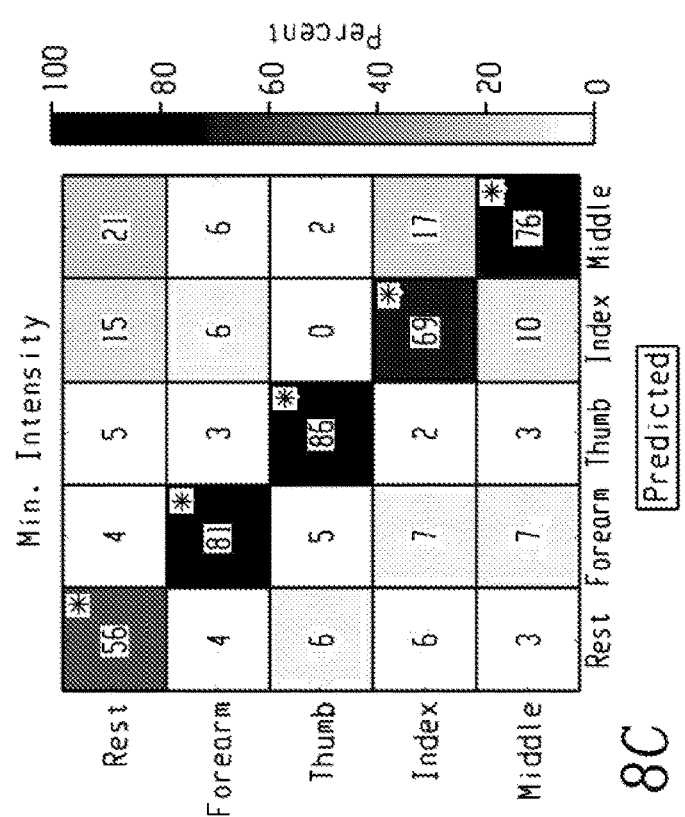
Figure 8C:
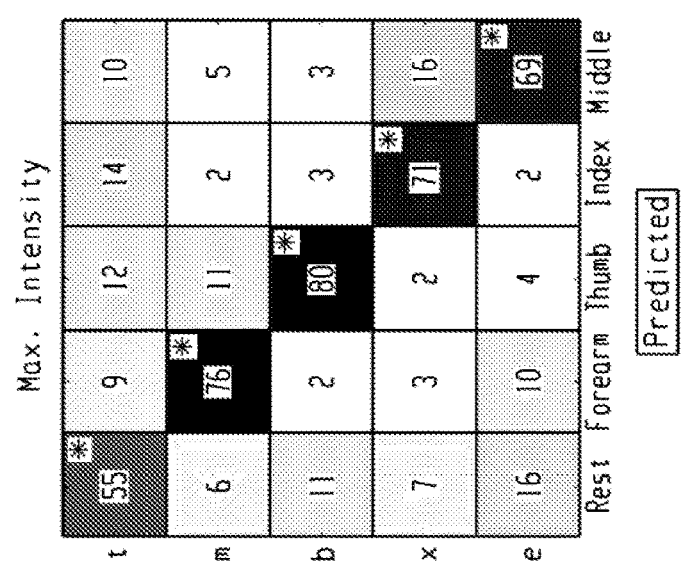

Next, experiments explored whether this sensory activity can be decoded from M1. Decodable sensory events could control a feedback device for improving the impaired sense of touch and subsequent upper limb sensorimotor function. A support vector machine (SVM) was trained to detect the skin region being passively stimulated (i.e., a 'passive sensory decoder'), given the underlying neural activity (FIG. 8A). Sensory stimulus location was reliably decoded from M1 across a period of several months, performing significantly above chance with low false positive rates (FIGS. 8B and 8C). Interestingly, decoders for locations that the participant can feel (forearm and thumb) performed equivalently to decoders for locations that the participant largely cannot feel (index and middle). This result demonstrates the ability to decode residual sensory neural activity that is below conscious perception, from functionally relevant hand dermatomes.

Figure 9A:
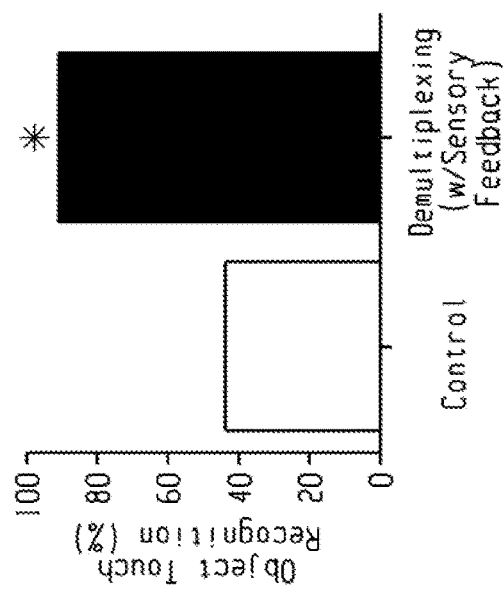
FIGS. 9A, 9B, 9C, and 9D illustrate aspects of experiments showing touch can be decoded from M1 to control closed-loop sensory feedback and enhance hand sensory function, as described herein.

Residual sensory activity could also be decoded using in a more challenging context during active object touch using a separate SVM (i.e., a 'touch decoder'; FIG. 9). During validation experiments, touch decoders were time locked to force application from the hand and performed with high responsiveness during object touch events (~85%; FIG. 9A, 'Touch'; $F[3,68]=209$, $p<0.0001$). FES alone or movement alone were control cues lacked object touch events, and did not activate the touch decoder, as expected (FIG. 9A, 'No Touch'). These results reveal that residual touch neural activity can be reliably decoded from M1 during active object manipulation.

Figure 9B:
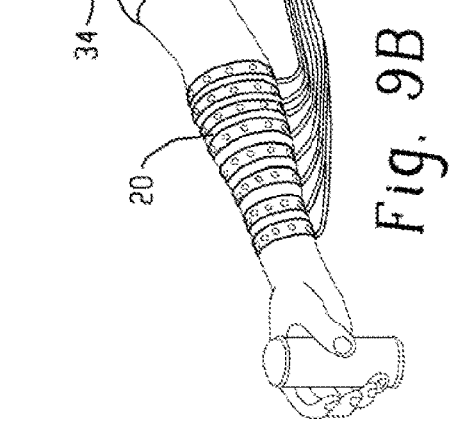
Figure 9C:
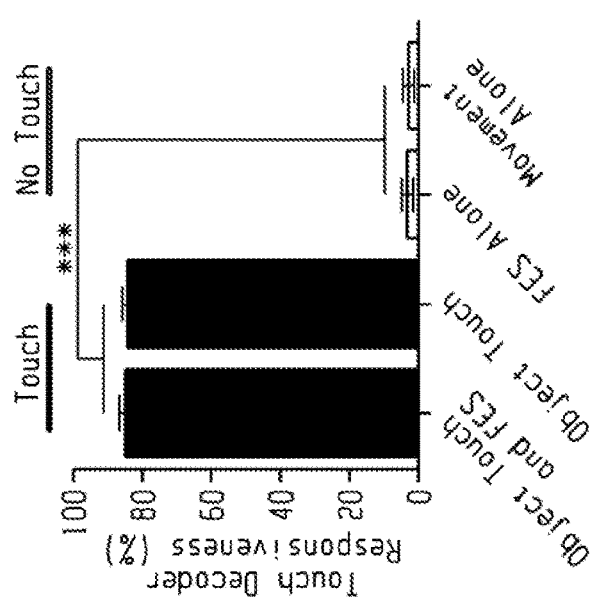

The participant was next interfaced with a vibrotactile array 34 on the right bicep (corresponding to the haptic device 34 of FIG. 1), to enable closed-loop sensory feedback (FIG. 9B; also showing an embodiment of the FES device 20 of FIG. 1). The vibrotactile array 34 was controlled in real time by a touch decoder, to enhance the perception of hand sensory events that are significantly impaired following SCI. The participant improved from a C5/C6 to a C8/T1 level of sensory perception using the closed-loop sensory feedback interface, enabling improved object touch recognition from below chance to an over 90% recognition rate (FIG. 9C, righthand bar; $t(20)=2.5$, $p=0.02$; FIG. 3D) compared to control (FIG. 9C, lefthand bar). These significant sensory improvements were driven by sub-perceptual sensory neural activity that is demultiplexed from M1 and transformed into conscious perception.

A still further set of experiments were performed to demonstrate that afferent and efferent activity in M1 can be simultaneously demultiplexed to control multiple devices, constituting a 'sensorimotor demultiplexing' BCI (FIG. 1). During a modified grasp and release test (GRT), the participant was first cued to position his hand around the object (FIG. 10A, cue at 0s), and then generate motor intention to activate FES to grasp and transfer the object (FIG. 10A, cue at 2s). The object touch decoder always preceded the motor intention decoder (FIGS. 10A and 10B), and was time locked to object touch as observed in video.

In some experiments, 'sensorimotor demultiplexing' BCI control was further enabled using the simultaneous decoding of touch and motor intention during a set of upper limb assessments. This closed-loop demultiplexing BCI system enabled significant improvements in sense of agency (FIG. 11A; $t(46)=3$, $p=0.004$), movement decoder latency (FIG. 11B, left side; $t(148)=2.9$, $p=0.004$), and GRT motor performance metrics (FIG. 11B, right side), compared to a motor-only BCI control. These results provide substantial evidence that sensory feedback during movement can enhance sense of agency and several other sensorimotor functions in patients with upper limb dysfunction. These findings demonstrate a BCI system that simultaneously demultiplexes afferent and efferent activity from human cortex to activate multiple assistive devices and enhance function.

The experiments demonstrate the ability to reanimate both motor and sensory function in a paralyzed and largely insensate limb. There are alternative ways to provide sensory feedback, including intracortical microsimulation (ICMS) in S1. Tactile-based feedback enables rapid sensory perception, significantly faster compared to artificial ICMS in S1. In the reported experiments it was chosen to use the participant's natural remaining sensory circuitry for touch decoding and address the need of SCI patients to use their own hand during upper limb activity.

BCIs provide a way to treat patients suffering from and array of functional deficits. Accurately and consistently decoding a control signal for a single assistive device is a significant challenge for BCIs. Embodiments disclosed herein extend capabilities of BCI technology to simultaneously decipher multiplexed afferent and efferent activity in M1 and control multiple devices simultaneously. Closed-loop sensory feedback also improved cognitive aspects of movement ownership, which is useful for sensorimotor performance. The experimental results show that sub-perceptual residual neural information can be reliably decoded from the human brain, and transformed to conscious perception to augment function.

The human cortex is generally modular and can encode a variety of stimuli or other activity. The sensory signal utilized in experiments reported herein may arrive in M1 directly, or from a separate source. Furthermore, evidence is accumulating that M1, and several other cortical modules, encode a multiplicity of features related to experience beyond their primary processing designation. In BCI applications contemplated herein, an array of control signals can potentially be demultiplexed from a single recording site, or multiple distributed interfaces. Advanced decoding strategies may be employed to decipher the multitude of representations encoded in neural activity and enabling demultiplexing BCIs. Regardless, the experimental results described herein present progress towards the design of next-generation human-machine interfaces capable of demultiplexing multimodal neural information for distributed device control and functional improvement.

Figure 6A:
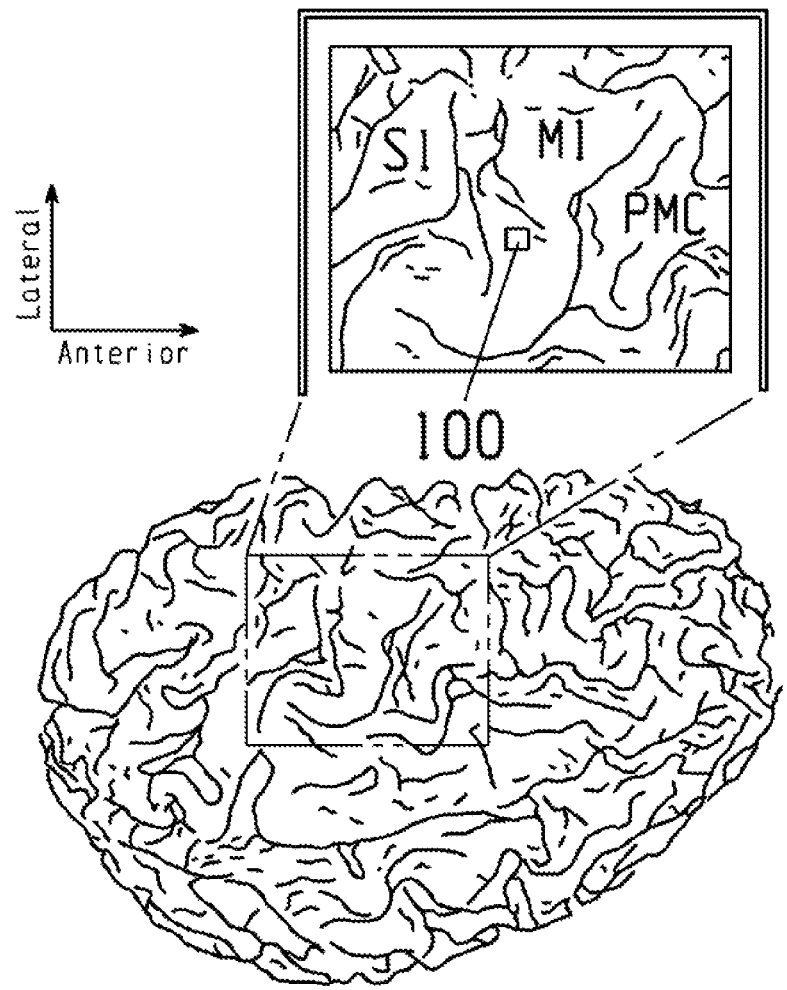
FIGS. 6A, 6B, 6C, 6D and FIGS. 7A and 7B illustrate aspects of experiments showing skin stimulation on the arm and hand evokes robust responses in contralateral primary motor cortex (M1) following cervical spinal cord injury (SCI) as described herein.
Figure 6B:
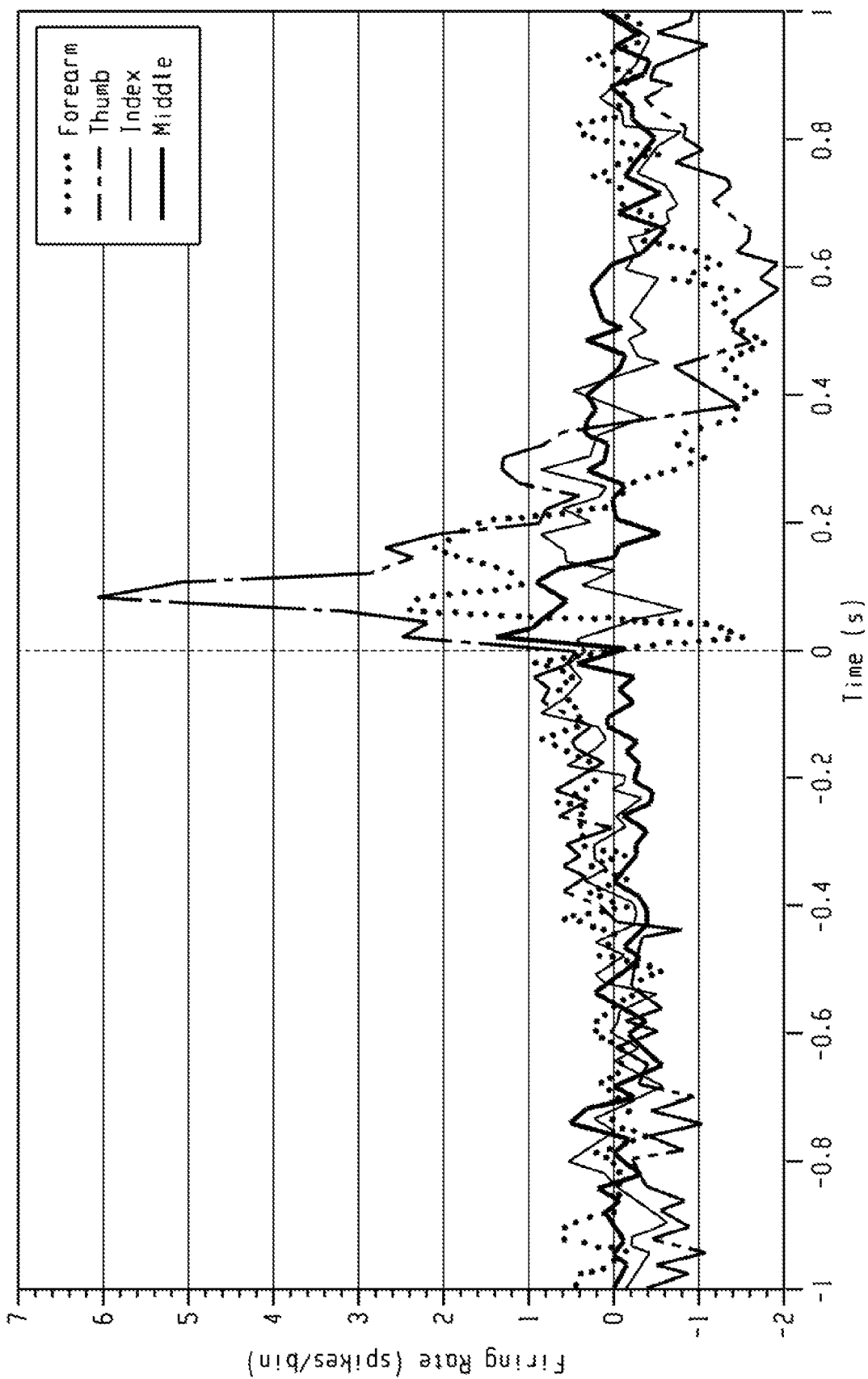
Figure 6C:
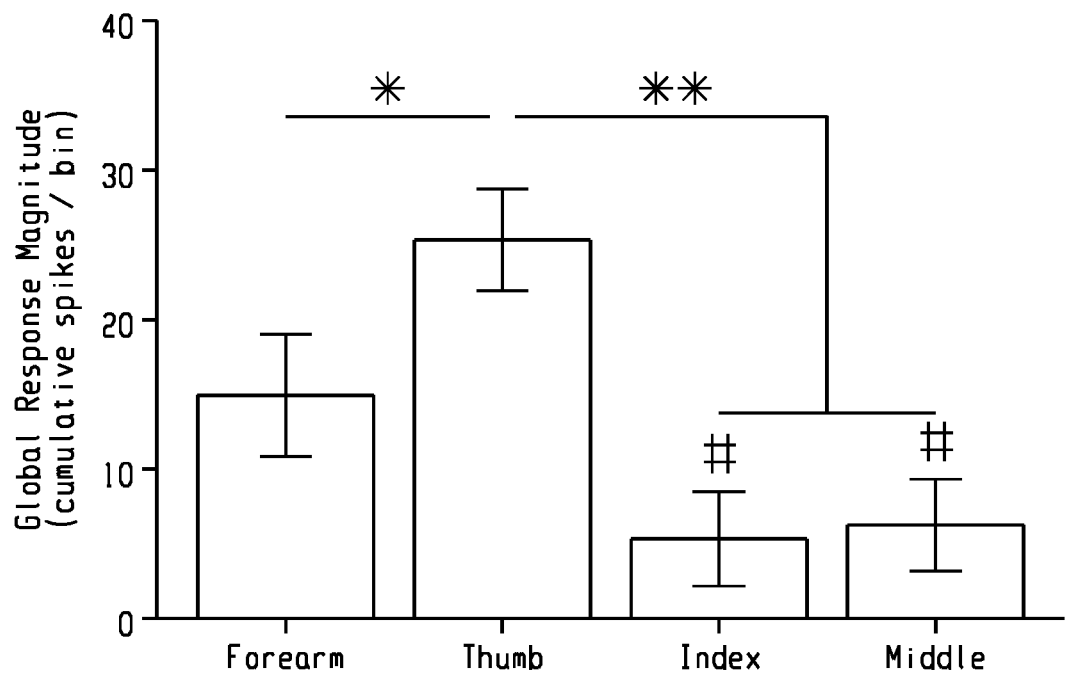
Figure 6D:
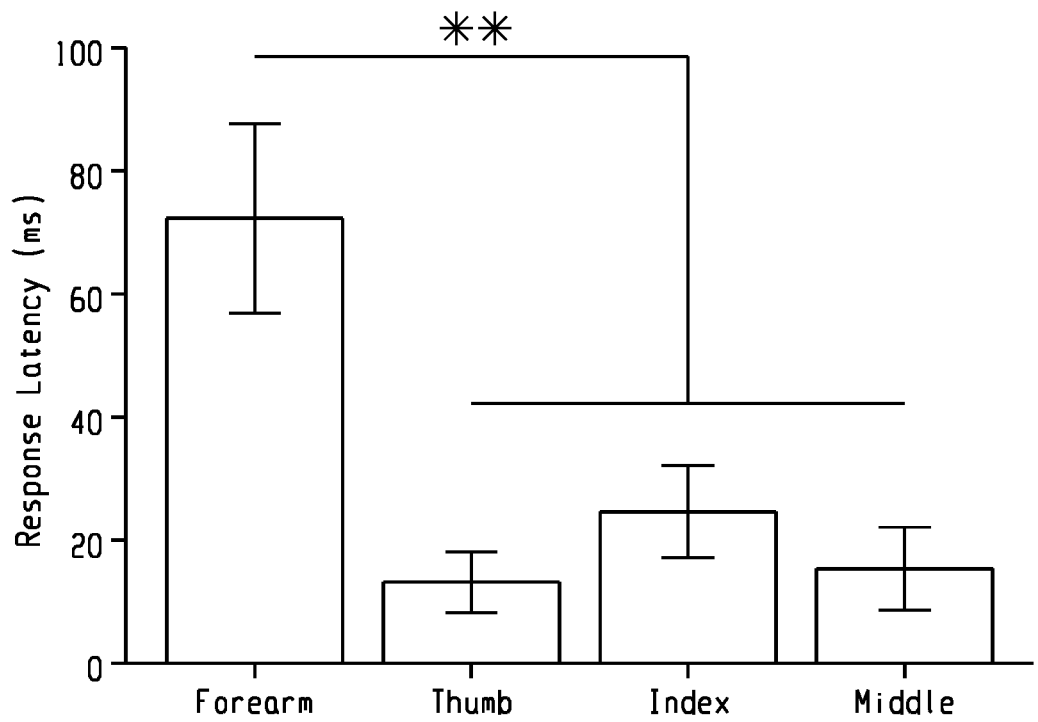

With particular reference to FIGS. 6A through 6D, aspects of experiments on skin stimulation on the arm and hand evoking robust responses in contralateral primary motor cortex (M1) following cervical spinal cord injury (SCI) are illustrated. In FIG. 6A, a three-dimensional reconstruction of the participant's cerebrum using T1 magnetic resonance imaging (MRI) images is shown. A box 100 depicts the microelectrode recording array implanted in left M1 (S1=primary somatosensory cortex; PMC=premotor cortex). In FIG. 6B, peri-stimulus time histograms were used to assess neural modulation in M1 (skin stimulation occurs at time 0, vertical dashed line). Stimulation of the forearm or thumb evoked time locked multi-unit activation, with smaller neural responses from index or middle. As seen in FIG. 6C, stimulation of the thumb evoked the largest response magnitude. As seen in FIG. 6D, stimulation of the thumb evoked the shortest response latency (* $=p<0.05$; ** $=p<0.01$; #=different from Forearm at $p<0.05$).

Figure 7A:
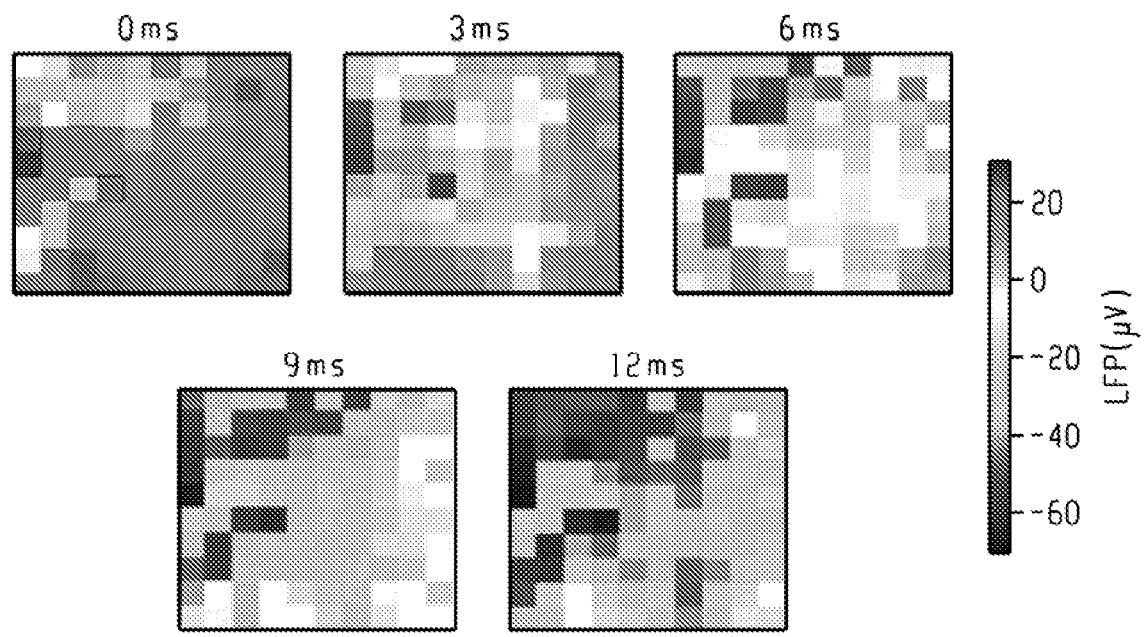
Figure 7B:
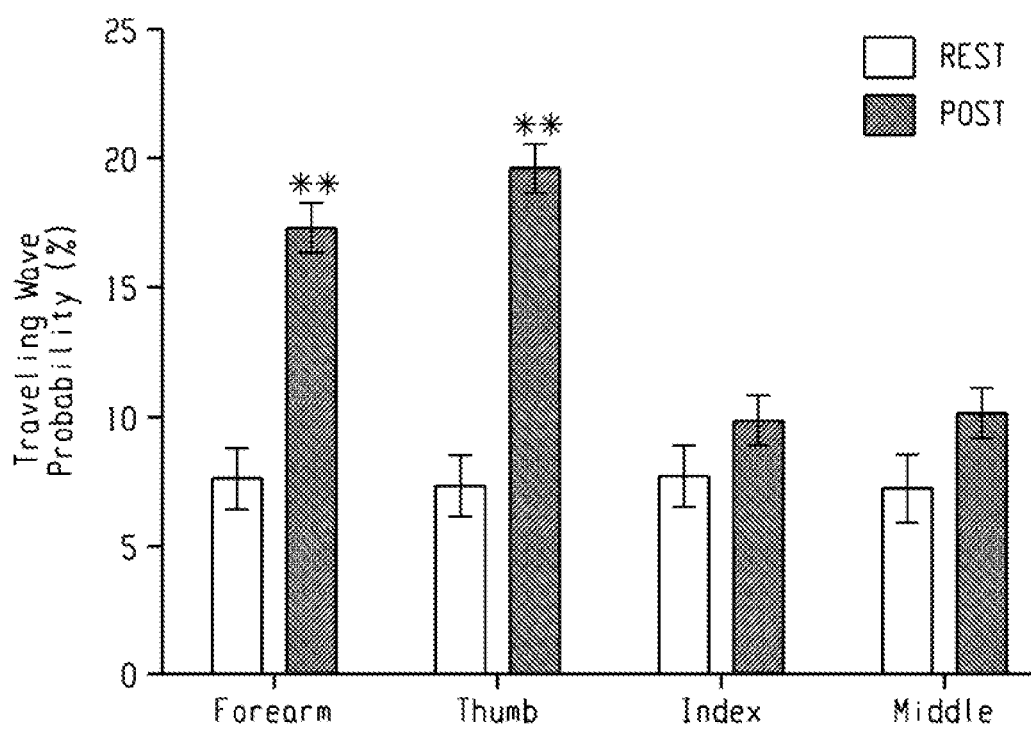

With particular reference to FIGS. 7A and 7B, skin stimulation also evoked traveling waves of activity propagating from S1 (left side of array) to PMC (right side of array) (5-20 Hz activity. FIG. 7A presents exemplar traveling wave front; color coded local field potential, $\mu V$). FIG. 7B presents traveling wave probability which significantly increased only following stimulation to semi-intact skin locations ( $=p<0.01$). These results illustrate that somatosensory stimuli evoke robust neural modulation in contralateral M1 following cervical SCI (data in FIGS. 6B, 6C, 6D, 7A, and 7B** is for the maximum stimulation intensity). Data presented are mean±S.E.M.

With particular reference to FIGS. 8A through 8C, aspects of experiments showing evoked sensory activity in M1 is decodable across skin locations are illustrated. FIG. 8A presents average color coded map of mean wavelet power (MWP) across all recording channels before, during, and after a sensory stimulus (MWP map for all Forearm stimuli; stimulus occurs at time 0). Support vector machine (SVM) decoders were built using MWP inputs from a recording at a given skin stimulation location (forearm, thumb, index, or middle) or for a rest period. These decoders reliably classified sensory stimulus location, demonstrating significant sensitivity above chance level with low false positive rates for both the maximum (as shown in FIG. 8B) and minimum stimulation intensities (as shown in FIG. 8C) (the confusion matrices of FIGS. 8B and 8C show color coded decoder values; * =significantly above chance at $p<0.001$). These results illustrate that sensory stimulus location can be demultiplexed from neural activity in M1.

Figure 9D:
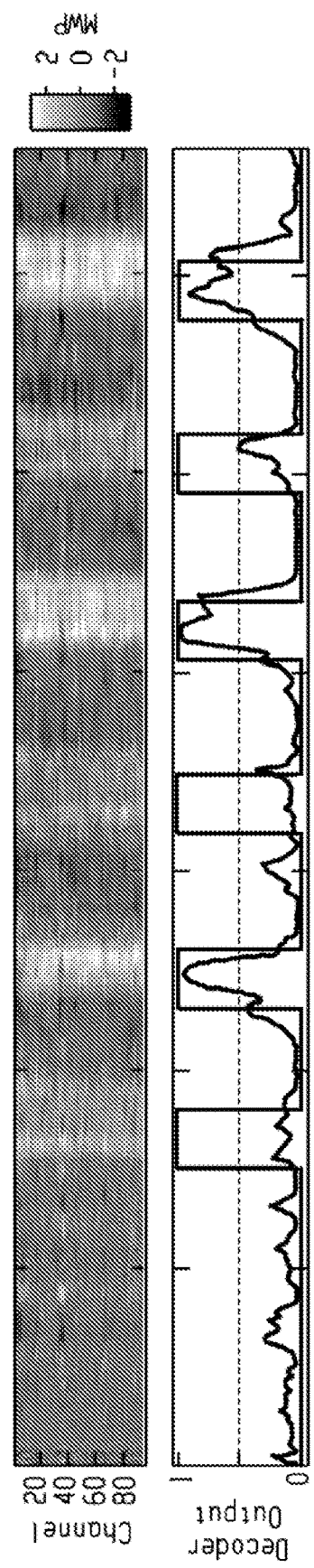

With particular reference to FIGS. 9A through 9D, aspects of experiments showing touch can be decoded from M1 to control closed-loop sensory feedback and enhance hand sensory function are illustrated. These experiments used neural data to construct a SVM touch decoder. During neural recordings, the participant systemically placed his hand onto a standardized can object, exposing the palmar hand regions to active object touch. With reference to FIG. 9A, SVM touch decoders were next validated, involving touch or no touch cues. Touch decoders responded with significantly higher responsiveness during object touch events (leftmost two bars of FIG. 9A), compared to FES alone (third bar from the right) or movement alone (rightmost bar) events lacking object touch. These results illustrate that machine learning algorithms can be trained on M1 activity to accurately demultiplex active object touch in M1 with minimal contribution from other sources. As diagrammatically shown in FIG. 9B, touch decoders next controlled closed-loop feedback via a vibrotactile array 34 around the sensate bicep skin. Closed-loop haptic feedback triggered by residual sensory information in M1 enhanced the participant's level of sensory perception from C5/C6 to C8/T1, and more than doubled object touch recognition during object grip (as seen in FIG. 9C, up to ~90%) (* $=p<0.05$). FIG. 9D presents exemplary color-coded mean wavelet power (MWP) input (top) and SVM decoder outputs (bottom) during the object touch recognition assessment (object placed on cues (vertical lines in the decoder output plot) 2, 4, & 6). These results demonstrate that residual sub-perceptual sensory neural information can be demultiplexed in M1 to trigger closed-loop feedback and significantly improve sensory function. Data presented are mean±S.E.M.

With particular reference to FIGS. 10A and 10B and FIGS. 11A and 11B, aspects of experiments showing afferent and efferent M1 activity can be simultaneously decoded to enable 'sensorimotor demultiplexing' BCI control and enhancement of sensorimotor function are illustrated. These experiments employed the experimental setup described previously with reference to FIG. 1 to perform a modified grasp and release test (GRT) task with the 'sensorimotor demultiplexing' BCI. Support vector machines were first trained to demultiplex afferent touch signaling (touch decoder) and efferent motor intention (motor decoder) from M1 activity. With reference to FIG. 10A, the touch decoder described herein with reference to FIGS. 9A through 9D was first challenged with a competing motor intention decoder (during a modified GRT). Touch decoders were triggered before motor decoders on all object transfers (time 0=start of cue). With reference to FIG. 10B, the touch decoder led the motor decoder by an average of 1.79±0.11 s. These results illustrate that afferent touch and efferent movement intention can be simultaneously demultiplexed from M1.

The touch decoder was next used to control closed-loop sensory feedback haptic device 34 (see FIG. 1) and enhance hand touch events. The motor decoder was used to control the FES device 20 of the arm (see FIG. 1) to produce hand movement. With reference to FIGS. 11A and 11B, closed-loop sensory feedback triggered by demultiplexed touch neural activity significantly improved the participant's sense of agency (FIG. 11A), movement decoder latency (FIG. 11B, left side), and GRT motor performance metrics (FIG. 11B, right side). These results demonstrate the ability to simultaneously decode afferent and efferent information from M1 and activate multiple assistive devices for augmenting sensorimotor function, constituting a 'sensorimotor demultiplexing' BCI (** $=p<0.01$). Data presented are mean±S.E.M.

Figure 12B:
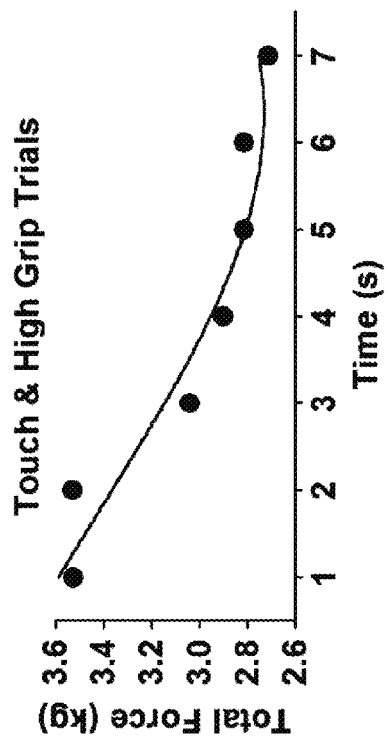
FIGS. 12A, 12B, and 12C illustrate aspects of experiments showing decoding of afferent grip intensity levels from M1 activity to enable limb reanimation regulated by touch.
Figure 12C:
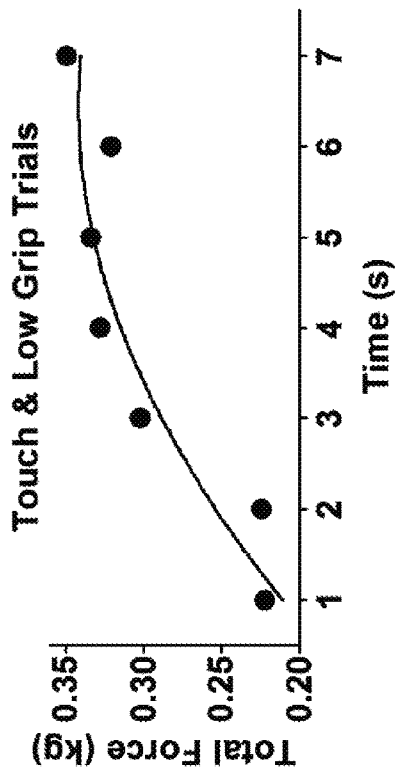
Figure 12A:
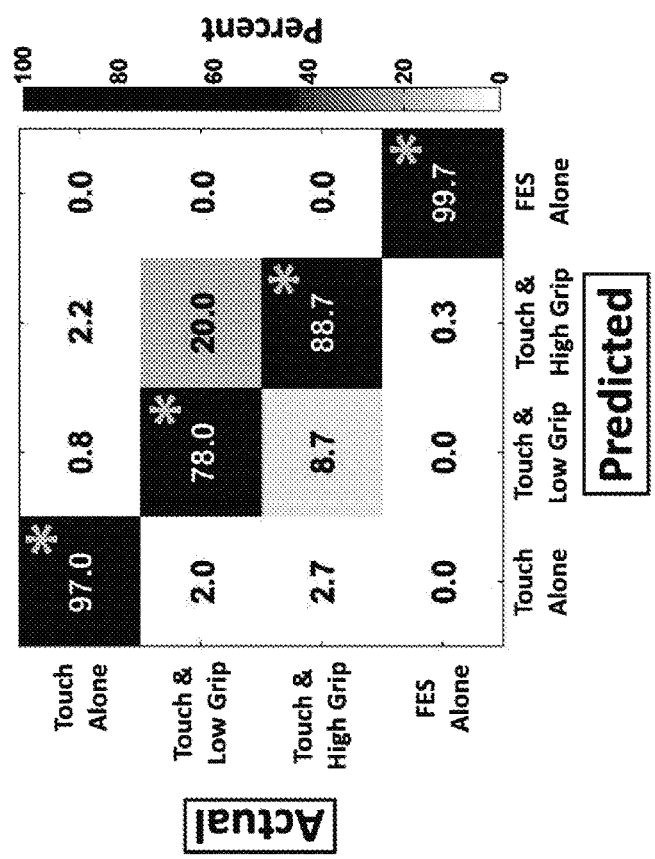

With particular reference to FIGS. 12A, 12B, and 12C, experiments are described which investigate decoding of afferent grip intensity levels from M1 activity to enable limb reanimation regulated by touch. These experiments address the burden on BCI users to control moment-to-moment movement using a constant decoded motor intention. Instead of constant motor intention, touch intensity signaling alone can potentially regulate limb reanimation during object grip. This capability could ensure appropriate BCI-mediated grip force application, while also freeing the BCI user's attention and visual stream for other important activities. Experiments were first performed to assess the hypothesis that multiple levels of afferent touch intensity signaling from the hand could be decoded from M1 activity. Grip force output was measured using a replicate of the standardized object with built in calibrated force sensors. Three different levels of afferent touch and grip intensity signals could be reliably decoded from M1 activity during object grip events with low false positive rates (overall ~87% responsiveness; FIG. 12A). As expected, touch and grip intensity decoders were not activated during control cues which did not have touch and grip events (see the "FES Alone" entries in FIG. 12A). Therefore, multiple levels of touch and grip intensity could be decoded from M1 activity.

As a proof of concept demonstration, the participant next enabled limb reanimation regulated by decoded afferent touch and grip intensity activity in M1. Trials were initiated at a high grip force (FIG. 12B, "Touch & High Grip" trials) or a low grip force (FIG. 12C, "Touch & Low Grip" trials) during a long duration grip of the object. Decoded "Touch & High Grip" served to decrease FES and grip force. Decoded "Touch & Low Grip" served to increase FES and grip force. During "Touch & High Grip" trials (FIG. 12B), grip force gradually decreased by a total of 810 grams (slope test: F=29, p=0.003). This was mediated by a decoder-controlled decrease in FES of 1.3 mA. During "Touch & Low Grip" trials (FIG. 12C), grip force gradually increased by a total of 120 grams (slope test: F=19, p=0.007). This was mediated by a decoder-controlled increase in FES of 0.4 mA. As expected, touch regulated grip forces initially exhibited an adjustment period followed by a steady state equilibration.

These results support the hypothesis that appropriate grip force regulation can be controlled by decoded afferent touch and grip intensity activity in M1. These results extend the "sensorimotor demultiplexing" BCI control results. "Touch regulated grip intensity" BCI control can be used to enable automated movement cascades, while simultaneously addressing the desire of patients with SCI to use their own hand. Overall, these results suggest that sensory discompleteness can be leveraged for multimodal restoration of touch and motor function.

Further details of the above-describe experiments are as follows. The participant was a 27-year-old male with a cervical SCI at C5/C6. A series of experiments were performed using either passive sensory stimulation (FIGS. 6A-6D, FIGS. 7A and B, and FIGS. 8A-C) or active object manipulation (FIGS. 9A-D, FIGS. 10A and 10B, FIGS. 11A and 11B, and FIGS. 12A, 12B, and 12C) to assess cortical neurophysiology, neural signal decoding, and assistive device control for upper limb functional improvement. All methods are separated into either passive sensory stimulation or active object manipulation experiments. All experiments were performed across a total of approximately 1 year. Approval for this study was obtained from the U.S. Food and Drug Administration (Investigational Device Exemption) and the Ohio State University Medical Center Institutional Review Board (Columbus, Ohio). The study met institutional requirements for the conduct of human subjects and was registered on the ClinicalTrials.gov website (Identifier NCT01997125; Date: Nov. 22, 2013). All experiments were performed in accordance with the relevant guidelines and regulations set by the Ohio State University Medical Center. The participant referenced in this work provided permission for photographs and videos and completed an informed consent process prior to commencement of the study.

As previously noted, the study participant was a 27-year-old male with stable, non-spastic C5/C6 quadriplegia from cervical SCI. He underwent implantation of a Utah 96 channel microelectrode array (Blackrock Microsystems, Inc., Salt Lake, Utah) in his left primary motor cortex. The hand area of motor cortex was identified preoperatively by fusing functional magnetic resonance imaging (fMRI) activation maps obtained while the patient attempted movements co-registered to the preoperative planning MRI. Neural data was acquired using a Utah microelectrode array (Blackrock Microsystems, Inc., Salt Lake City, Utah) and the Neuroport neural data acquisition system. Recorded data from all 96 array channels was sampled at 30 kHz and band pass filtered online from 0.3-7.5 kHz using a third order Butterworth analog hardware filter. The neural data was then digitized and sent to a PC for saving or further on-line processing using a custom interface in MATLAB 2014a (The MathWorks; Natick, MA).

Neural signal conditioning and decoding using SVMs was done as follows. We used stimulation artifact removal, mean wavelet power (MWP) estimation, and non-linear SVM. FES-induced stimulation artifacts were detected by threshold crossings of 500 µV occurring simultaneously on at least 4 of 12 randomly selected channels. A 3.5 ms window of data around each detected artifact was then removed and adjacent data segments were rejoined. This approach leaves the vast majority of the neural data intact. A series of control experiments confirmed the removal of the stimulation artifact across several contexts. Data collected demonstrates the robust ability to remove artifacts from the data with this approach prior to signal analysis.

Neural activity was next measured using MWP. Wavelet decomposition was applied to the raw voltage data, using the 'db4' mother wavelet and 11 wavelet scales. Four wavelet scales 3-6 were used, corresponding to the multiunit frequency band spanning approximately 234 to 3,750 Hz. The mean of the wavelet coefficients for each scale of each channel was calculated every 100 ms and a 1 s wide boxcar filter was applied to smooth the data. Baseline drift in the data was estimated by using a 15 s boxcar filter and was subtracted from the smoothed mean wavelet coefficients for the corresponding 100 ms window. The mean coefficients were then standardized per channel, per scale, by subtracting the mean and dividing by the standard deviation of those scales and channels during the training blocks. The four scales were then combined by averaging the standardized coefficients for each channel, resulting in 96 MWP values, one for each electrode in the array, for every 100 ms of data. The resulting MWP values were used as input into the given non-linear SVM decoders. The SVM model training and testing methods are detailed below for both the passive sensory stimulation or active object manipulation experiments.

The embodiment of the FES device 20 used in the experiments to stimulate the arm musculature and produce movement consisted of a multi-channel stimulator and a flexible cuff with up to 130 electrodes that is wrapped around the participant's forearm. During use, hydrogel disks (Axelgaard, Fallbrook, CA) were placed between the electrodes and skin to act as a conduction enhancer. The electrodes are 12 mm in diameter and were spaced at 22 mm intervals along the longitudinal axis of the forearm and 15 mm intervals in the transverse direction. Current-controlled, monophasic rectangular pulses (50 Hz pulse rate and 500 µs pulse width) were used to provide electrical stimulation. Pulse amplitudes ranged from 0 to 20 mA and were updated every 100 ms. Stimulator calibrations were performed for each movement using an anatomy-based trial-and-error method to determine appropriate electrode spatial patterns.

In passive sensory stimulation experiments, we first assessed evoked neural activity in left primary motor cortex M1 using bi-polar electro-tactile stimulation at skin locations on the participant's arm and hand. Electro-tactile stimulation was chosen in part for its safety and precise electronic control of stimulus features, and its ability to evoke activity in M1 following from pilot recordings. We targeted four skin locations innervated by the spinal cord above, at, and below the participant's C5/C6 SCI. The skin stimulation locations were: (1) C5 dermatome (forearm; electrode location: skin above the extensor carpi radialis longus); (2) C6 dermatome (thumb; electrode location: skin above the distal phalanx of digit 1); (3) C7 dermatome (index; electrode location: skin above the distal phalanx of digit 2); and (4) C7 dermatome (middle; electrode location: skin above the distal phalanx of digit 3). The notation: "Forearm", "thumb", "index", and "middle" are used to describe these four skin stimulation sites. A subset of control recordings were also performed on the opposite arm ipsilateral to the M1 implant for the homotopic thumb and forearm locations. Cutaneous landmarks and/or ink markings were used throughout as needed to confirm skin stimulation locations. The participant wore an eye mask and ear plugs during all passive sensory stimulation experiments to significantly reduce any external visual and auditory events during recordings. Recordings were video recorded and performed under the supervision of a licensed physiatrist.

The stimulation interface for a given skin location consisted of a pair of hydrogel disk electrodes adhered to a modified version of the FES interface used in our previous studies. Each hydrogel disk electrode (Axelgaard, Fallbrook, CA) is 12 mm in diameter, 1.27 mm thick, spaced by ~2-3 mm, and attached to a metal electrode consisting of copper with an electroless nickel immersion gold coating embedded in the polyimide flex circuit. We used two current levels of stimulation: minimum intensity=2.4 mA, and maximum intensity=9.6 mA (current controlled stimulation, monophasic rectangular pulses, 50 Hz, 500 µs pulse width, 100 ms train duration). Stimulation intensity was selected based on our pilot studies to apply stimulation sufficient to evoke activity in M1 (minimum intensity) and up to an intensity below a noxious level (maximum intensity). Fifty replicates of stimulation were performed within a given recording with an inter-stimulus interval of 2 s, to ensure the relaxation of neural activity similar to our previous studies. On a given recording day, 2-3 skin stimulation locations were randomly selected for stimulation and simultaneous neural recordings. The amplitudes of current for a given skin stimulation location were also randomly selected for a given location. Recordings were performed across a total of ~5 months to assess the chronic viability of the evoked neural signal.

Experiments on evoked activity analyses are next described. In Peri-Stimulus Time Histograms (PSTHs) experiments, all neural recordings were analyzed offline using MATLAB 2016b (The MathWorks). Following stimulation artifact removal, the signal was band-passed filtered (3rd order Butterworth filter; 300-3000 Hz). Single and multi-unit activity was classified off-line using superparamagnetic clustering. Single units were in addition manually inspected, similar to previous studies. For each channel, the neural activity was first binned (20 ms bin width). PSTHs were then constructed for the neural data 1 second before and after stimulation to assess evoked responses similar to previous studies. A positive 95% confidence interval (C.I.) was then applied to the given channel's PSTH to identify significant neural modulation. For channels with a significant evoked response (i.e., a positive 95% C.I. crossing), we calculated the response magnitude (units: cumulative spikes above the 95% C.I., minimum of 3 consecutive bins needed) and response latency (the first significant bin, units=ms). The global response magnitude was then estimated using the cumulative sum of response magnitudes across array channels for the given condition. We report the global response magnitude (see FIG. 6C) and response latency (FIG. 6D).

Experiments on Local Field Potential Spectrograms and Spatiotemporal Organization were also performed. The local field potential (LFP) was first generated (3rd order Butterworth filter; 1-300 Hz). Spectrograms were next constructed from the LFP to assess low frequency neural modulations during passive sensory stimuli (using 'spectrogram' in MATLAB). LFP from 5-20 Hz exhibited robust time-locked modulation during sensory stimuli, corresponding to a well-studied sensorimotor frequency band. The 5-20 Hz LFP band was therefore used for the following analyses on spatiotemporal organization of the evoked response. For each channel, all 5-20 Hz LFP oscillations were first extracted for analysis, and further classified as occurring during either REST (15 s period of spontaneous activity, prior to stimulation) or 1 s after a sensory stimulus (POST). We separated the positive and negative phases of all LFP oscillations to assess the hyperpolarized and depolarized components of the oscillatory activity. The temporal order (i.e., rank) of LFP time to peak was then calculated across all channels for a given recording to assess the spatiotemporal organization of the activity (score of 1: first channel active; through a score of 96: last channel active; modified from reference 40). The cumulative score across all stimuli was then converted to a normalized probability, corresponding to the given channel's preferred order of activation. Each channel's temporal order probability was assessed separately for REST and POST. This spatiotemporal analysis illustrates that stimuli evoke a spatiotemporally organized response across the recording array, potentially identifying a putative source of the evoked response.

To assess potential evoked traveling waves, we again used all 5-20 Hz LFP oscillations for both positive and negative phases during the REST and POST stimulus periods. We utilized LFP peak analyses, gradient mapping of the LFP vector representation, and subsequent directionality of oscillatory activity, similar to previous studies on traveling waves and wave-like propagating neural activity. For each extracted LFP oscillation, we generated a velocity vector map across the recording array, assessing the magnitude and direction of the activity for each channel. Next, we transferred each channel's vector onto a phase plot for directionality averaging and subsequent directional statistics. Finally, we computed the given oscillation's circular variance and grand directionality vector (i.e., resultant vector), averaged over all 96 channels using the circular statistics toolbox for MATLAB. Oscillations with low circular variance have a more prominent preferred directionality and spatial organization across the array, compared to oscillations with a higher circular variance. The circular variance values for all oscillations during REST and POST were then binned for the given recording, to assess a potential effect of sensory stimulation on preferred directionality changes in the evoked response across time (20 ms bin width). Oscillations with a circular variance less than the negative 95% confidence interval for the given recording were considered traveling waves. We report the grand directionality vector and the corresponding traveling wave probability for all sensory recordings.

In experiments on decoding passive sensory stimulation, a nonlinear SVM classifier was used to decode stimulus location for the passive sensory stimulation recordings at both a low and high stimulation intensity (SVM hyperparameters: $\gamma=0.001$, $C=1$). Two SVM models (low and high stimulation intensity) were each built with 5 classes: Rest, Forearm, Thumb, Index, and Middle. The input features for each model were calculated as follows: (1) We recorded neural activity and calculated MWP during ~350 total stimuli for each stimulus intensity and skin location across ~5 months; (2) MWP was standardized across blocks within each day to account for day-to-day variability; (3) For each skin stimulation trial, defined by 0.2 s before and 0.8 s after a given sensory stimulus (this epoch was chosen due to the robust neural modulation that occurs during this time period around the stimulus, see FIGS. 6B and 7A), MWP was vectorized to a 960-feature vector (96 channels*10 bins; where each bin spanned 100 ms); The same MWP vectorization process was applied to 350 randomly selected 1 s samples of Rest data collected during spontaneous activity in the first 15 s of a given recording; and (4) For each class, the vectorized MWP was shuffled to remove any effect of stimulus order or recording time during the ~5-month period and equally assigned to either training or testing data (~175 trials per class for training; ~175 trials per class for testing). We report SVM model performance as a confusion matrix (see FIGS. 8B and 8C; diagonal values=sensitivity; off-diagonal values=false positive rate). Sensitivity is calculated as the percentage of correctly predicted class labels for the targeted class (true positive rate). False positive rate is calculated as the percentage of incorrectly predicted class labels for a given off-target class. Rows represent the actual recorded class, while the columns represent the model's predictions.

Some further aspects of the active object manipulation experiments are next described. For clinical assessment of sensory function, monofilament testing was performed by a licensed physiatrist to evaluate the participant's hand sensory function (GRASSP assessment, Semmes-Weinstein monofilaments; Toronto, ON). The palmar and dorsal aspects of digits 1 (thumb), 2 (index), and 3 (middle) were exposed to multiple trials of either 0.4, 2, 4, or 300 g of force while the participant was blind-folded. Trial location and force level were randomized. The participant was asked to report the application of the applied tactile stimulus. The following scores were generated to quantify the participant's tactile acuity: 4=0.4 g detection at 66%; 3=2 g at 33%; 2=4 g at 33%; 1=300 g at 33%; 0=300 g at 0%. The participant uses his hand to manipulate objects during BCI operation. We assessed the participant's ability to recognize object touch during FES-mediated and grip (standardized objects tested from the Action Research Arm Test: small cylinder (1 cm diameter) and large cylinder (2 cm diameter)). The participant was again blind-folded, and the object was placed between digits 1 and 2 without touching the skin on randomized cues where a grip was triggered (small cylinder: lateral pinch grip; large cylinder: can grip). The given grip was cued for a duration of 3 seconds. The participant then reported whether there was an object in his hand. Each grip cue was bounded by rest cues with random durations between 5 to 6 seconds. We report Object Touch Recognition as the percentage of cues the participant correctly identified there was an object present during the grip for each object.

In experiments on decoding active touch, we trained SVM decoders to recognize active hand touch events in real-time. These decoders were trained using neural data during active object touch, in contrast to the passive sensory stimulation decoders described above (see Decoding Passive Sensory Stimulation). We used the can object, a part of the standard clinical grasp and release test battery (5.4×9.1 cm). For model training, we recorded 9 total cues of labeled touch data, with each cue consisting of a 6 second period. Cues were conveyed by a virtual hand on a computer monitor. Each cued period of touch data was bounded by rest cues with random durations between 5 to 6 seconds. For each touch cue period, the participant first moved his hand down onto and around the can object for 3 seconds, followed by a scripted object grip period for an additional 3 seconds where functional electrical stimulation (FES) triggered a more forceful grip. Therefore, touch decoder model training consisted of neural data during: 1) movement onto the object, 2) natural touch of the object, and finally 3) additional FES mediated touch. This touch decoder model was then tested on 4 cue types to assess model performance during 'touch' and 'no touch' events. The participant completed the following cued events: (1) 3 seconds of natural touch of the object followed by 3 seconds FES mediated touch ('Touch'), (2) 6 seconds of natural object touch ('Touch'), (3) 6 seconds of identical movement without the object present ('No Touch'), (4) 6 seconds of FES without the object present ('No Touch'). For this touch decoder testing, we report model responsiveness during the 4 cue types, defined as the percentage of time the touch decoder output was above the activation threshold during the given cue (activation threshold=0.5). This touch decoder was then used to trigger the closed-loop haptic feedback interface 34 during object manipulation. In a subset of experiments, we also assessed touch decoder timing during simultaneous recording of applied force (force transducer interface: custom designed piezoresistive sensor pad (FlexiForce; Boston, MA) interfaced with an Arduino Mega 2560 board transferring force data to the PC).

For decoding movement intention, we built movement decoders for manipulating the can object (a part of the grasp and release test). Briefly, the participant was prompted to imagine performing a can grip and movement, using a virtual hand displayed on a computer monitor. Each movement cue lasted 3-4 seconds, and was bounded by rest cues with random durations between 5 to 6 seconds. During a movement cue, FES triggered the can grip. FES was controlled by the SVM movement decoder starting after the first 3 movement cues. This motor decoder model was updated during subsequent training cues until a sufficiently accurate model was built (accuracy>~80%). This motor decoder was then used to control FES during object manipulation.

In experiments employing the haptic device 34, this embodiment of the haptic feedback interface 34 consisted of 3 low-noise vibrotactile coin motors affixed to a velcro band wrapped around the participant's right bicep (coin motor details: 12 mm diameter, 3.4 mm height, 2.6 G force output; Need for Power; Shenzhen, Guangdong, China). This interface was tethered to an Arduino Mega 2560 board to power and control vibrotactile haptic feedback. Haptic feedback interfaces targeting the skin over the biceps have been used in several sensory feedback studies and is well studied. Our pilot data confirm that the participant's right bicep exhibited normal sensory function, and haptic stimulation was recognized on 100% stimuli. The interface was designed to ensure participant comfort during movement. The vibrotactile motors achieved maximum amplitude (2.6 G) within 1 ms of controller signal initiation. All haptic feedback interface communication was also recorded. This haptic feedback interface was controlled by the touch decoders outlined above and was triggered in real time during closed-loop sensory feedback tasks that employed the haptic device 34.

Experiments investigating functional improvement with and without closed-loop haptic feedback were performed as follows. We assessed upper limb function across a battery of four clinical assays under the supervision of a licensed physiatrist. The haptic feedback interface 34 was placed on the participant's right bicep during all assessments, and function was assessed across trials during either a 'no haptics' or 'haptics' condition. The 'no haptics' condition consisted of functional testing without any vibrotactile sensory feedback. 'Haptics' consisted of on demand touch decoder controlled closed-loop sensory feedback for rapidly conveying hand touch events back to the user. The participant was blinded to the sensory feedback condition before a series of assessment trials. All clinical assays were performed across 2 clinical testing days. The first clinical assessment was an extension of the monofilament testing. A touch decoder was first constructed as previously described. The palmar and dorsal aspects of digits 1-5 were exposed to multiple trials of either 0.4, 2, 4, or 300 g of force while the participant was blind-folded. Trial location and force level were randomized. The participant was asked to report the application of the applied tactile stimulus. During the 'haptics' condition, the touch decoder controlled haptic feedback. Haptic feedback time locked to mechanical stimulation was reported by the participant and constituted a positive report of skin stimulation. All trials were recorded with high speed video for offline analysis.

The second clinical assessment was an extension of the Object Touch Recognition test. The standardized large cylinder object was used. A touch decoder was first constructed as previously described. The participant was again blind-folded, and the object was placed between digits 1 and 2 without touching the skin on randomized cues where a grip was triggered by FES during shuffled series of 'haptics' or 'no haptics' conditions. Grip was cued for a duration of 3 seconds. The participant then reported whether there was an object in his hand. Each grip cue was bounded by rest cues with random durations between 5 to 6 seconds. We again report Object Touch Recognition as the percentage of cues the participant correctly identified there was an object present during grip.

The third clinical assessment consisted of the modified grasp and release test (GRT) only using the can object. A touch decoder and movement decoder was constructed as previously described. The participant was then cued to repeatedly grasp, move, and release the object during shuffled series of 'haptics' or 'no haptics' condition trials. After each GRT trial, the participant reported his sense of agency (SoA) (i.e., "How in control did you feel of the movement and grip?"). The SoA score ranged from 0-100, similar to previous studies (0=poor sense of control; 100=perfect sense of control).

The fourth clinical assessment was a modified GRT again using only the can object. A touch decoder and movement decoder was constructed as previously described. The participant was instructed to grasp, transfer, and release the can object onto an elevated platform as fast as possible repeatedly during shuffled series of 'haptics' or 'no haptics' condition trials. Each GRT assessment period consisted of two 60 second movement periods separated by a 20 second rest period. All GRT trials were recorded with high speed video for offline analysis. We report the number of objects successfully transferred during the movement periods. We also assessed the interval between the touch decoder and movement decoder to examine the neurophysiological substrates of GRT performance with and without haptic feedback (high speed video was also used in addition to decoder times to confirm touch and movement event start times). The touch or movement event start time was calculated across GRT trials using the time each decoder crossed the significance threshold to trigger the respective assistive device (decoders were normalized from 0-1; significance threshold=0.5). We report the interval (s) between the touch and movement decoder.

Some further aspects of the data analysis and statistics are as follows. Normality tests were performed for each analysis to determine if parametric or nonparametric statistics should be used. All statistical tests were two-tailed and performed in MATLAB 2016b. An alpha level of 0.05 was accepted for significance unless Bonferroni corrections are noted. Effects of sensory stimuli on evoked M1 neural activity were evaluated using separate one-way ANOVAs for the minimum and maximum stimulation intensities. The factor was skin location with 4 levels: forearm, thumb, index, and middle. Tukey's post-hoc test was used to determine differences in response magnitude and response latency across skin locations (see FIGS. 6C and 6D). Effects of skin stimulation on spatiotemporal response organization were evaluated using independent samples t-tests for both the response latency topography and traveling wave probability data. Effects of skin stimulation on preferred directionality vector magnitudes was assessed using circular statistics.

A one-sided t-test was used to determine if decoder performance values were above chance for the passive sensory stimulation data (confusion matrices, see FIGS. 8B and 8C). Each confusion matrix value was compared to a chance prediction level for statistical evaluation. Chance levels were generated by randomly permuting the data labels 10 times. Values from unrandomized label permutation were then compared with values from randomized label permutation. A Bonferroni corrected alpha value of 0.002 was used for significance (0.05/25 comparisons).

For the active object manipulation experiments, touch decoder responsiveness values were assessed using a one-way ANOVA. The factor was cue type with four levels: Object Touch & FES, Object Touch, FES alone, and Movement alone. Tukey's post-hoc test was used to determine differences in touch decoder responsiveness across cue type. Functional improvement assessments were performed across two separate clinical testing days for the following total trial counts: object touch recognition: 36 trials (for either 'haptics' and 'no haptics'), SoA: 24 trials (for either 'haptics' and 'no haptics'), GRT performance & decoder interval: 77 trials ('haptics') and 73 trials ('no haptics'). Effects of closed-loop haptic feedback were assessed using independent samples t-tests for the object touch recognition, SoA, GRT performance, and decoder interval data, comparing the 'no haptics' to 'haptics' conditions.

The preferred embodiments have been illustrated and described. Modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. An apparatus for assisting a patient having a spinal cord injury, the apparatus comprising:
   an electrical brain signal monitoring interface configured to record at least one electrical brain signal of the patient;

a functional electrical stimulation (FES) device configured to connect via FES electrodes with a paralyzed portion of the patient that is paralyzed due to the spinal cord injury and to control the paralyzed portion of the patient by applying FES to the paralyzed portion of the patient via the FES electrodes;

an electronic processor operatively connected with the electrical brain signal monitoring interface to receive the at least one electrical brain signal and with the FES device to control the FES applied to the paralyzed portion of the patient; and a non-transitory storage medium storing instructions readable and executable by the electronic processor, the instructions including:

electrical brain signal demultiplexing instructions that are executable by the electronic processor to demultiplex the at least one electrical brain signal into an efferent motor intention signal output by the brain and at least one afferent sensory signal received at the brain; and FES control instructions that are executable by the electronic processor to control the FES applied to the paralyzed portion of the patient by the FES device based on at least the efferent motor intention signal.

2. The apparatus of claim 1 wherein the electrical brain signal demultiplexing instructions are executable by the electronic processor to demultiplex the at least one electrical brain signal into the efferent motor intention signal and the at least one afferent sensory signal including at least an afferent proprioception sense signal generated by a proprioception sense of the paralyzed portion of the patient.

3. The apparatus of claim 2 wherein the FES control instructions are executable by the electronic processor to control the FES applied to the paralyzed portion of the patient by the FES device based on at least the efferent motor intention signal and the afferent proprioception sense signal.

4. The apparatus of claim 2 wherein the paralyzed portion of the patient includes a hand, and the FES control instructions are executable by the electronic processor to:

determine an orientation of a palm or wrist of the patient based on the afferent proprioception sense signal; and control the FES applied to orient the hand to grasp an object based on the determined orientation and then control the FES to cause the hand to grasp the object.

5. The apparatus of claim 1 wherein the FES control instructions are executable by the electronic processor to control the FES applied to the paralyzed portion of the patient by the FES device based on the efferent motor intention signal and not based on the at least one afferent sensory signal.

6. The apparatus of claim 1 wherein the FES device comprises an FES cuff configured to connect via FES electrodes with a paralyzed arm, hand, leg, or foot of the patient that is paralyzed due to the spinal cord injury and to control the paralyzed arm, hand, leg, or foot of the patient by applying FES to the paralyzed arm, hand, leg, or foot via the FES electrodes.

7. The apparatus of claim 1 wherein the electrical brain signal demultiplexing instructions are executable by the electronic processor to apply a machine learning component to demultiplex the at least one electrical brain signal into the efferent motor intention signal and the at least one afferent sensory signal.

8. A non-transitory storage medium storing instructions readable and executable by an electronic processor that is operatively connected to receive at least one electrical brain signal from a patient and to operate a functional electrical stimulation (FES) device to apply FES to control a paralyzed portion of the patient that is paralyzed due to a spinal cord injury of the patient, the stored instructions including:

electrical brain signal demultiplexing instructions that are executable by the electronic processor to demultiplex the at least one electrical brain signal into an efferent motor intention signal and at least one afferent sensory signal including at least an afferent proprioception sense signal generated by a proprioception sense of the paralyzed portion of the patient; and FES control instructions that are executable by the electronic processor to control the FES applied to the paralyzed portion of the patient by the FES device based on at least the efferent motor intention signal.

9. The non-transitory storage medium of claim 8 wherein the FES control instructions are executable by the electronic processor to control the FES applied to the paralyzed portion of the patient by the FES device based on at least the efferent motor intention signal and the afferent proprioception sense signal.

10. The non-transitory storage medium of claim 8 wherein the paralyzed portion of the patient includes a hand, and the FES control instructions are executable by the electronic processor to:

determine an orientation of a palm or wrist of the patient based on the afferent proprioception sense signal; and control the FES applied to orient the hand to grasp an object based on the determined orientation and then control the FES to cause the hand to grasp the object.

11. The non-transitory storage medium of claim 8 wherein the FES control instructions are executable by the electronic processor to control the FES applied to the paralyzed portion of the patient by the FES device based on the efferent motor intention signal and not based on the at least one afferent sensory signal.

12. The non-transitory storage medium of claim 8 wherein the electrical brain signal demultiplexing instructions are executable by the electronic processor to apply a machine learning component to demultiplex the at least one electrical brain signal into the efferent motor intention signal and the at least one afferent sensory signal.

13. A method comprising:

receiving at least one electrical brain signal from a patient;

by an electronic processor, demultiplexing the at least one electrical brain signal into an efferent motor intention signal and at least one afferent sensory signal; and by the electronic processor, controlling a functional electrical stimulation (FES) device to apply FES to control a paralyzed portion of the patient that is paralyzed due to a spinal cord injury of the patient;

wherein the controlling of the FES device is based on the efferent motor intention signal and is not based on the at least one afferent sensory signal.

14. The method of claim 13 wherein the demultiplexing comprises demultiplexing the at least one electrical brain signal into the efferent motor intention signal and the at least one afferent sensory signal including at least an afferent proprioception sense signal generated by a proprioception sense of the paralyzed portion of the patient.

15. The method of claim 14 wherein the controlling of the FES device is based on at least the efferent motor intention signal and the afferent proprioception sense signal.

16. The method of claim 14 wherein the paralyzed portion of the patient includes a hand, and the controlling of the FES device includes:

determining an orientation of a palm or wrist of the patient based on the afferent proprioception sense signal; and
controlling the FES applied to orient the hand to grasp an object based on the determined orientation and then control the FES to cause the hand to grasp the object.

* * * * *